United States Patent [19]

Ganguly et al.

[11] Patent Number: 5,439,916

[45] Date of Patent: Aug. 8, 1995

[54] POLYCYCLIC QUINOLINE, NAPHTHYRIDINE AND PYRAZINOPYRIDINE DERIVATIVES

[75] Inventors: Ashit K. Ganguly, Montclair; Richard J. Friary, West Orange; John H. Schwerdt, Lake Hiawatha; Marvin I. Siegel, Woodbridge; Sidney R. Smith, Ridgewood; Edmund J. Sybertz, South Orange, all of N.J.

[73] Assignee: Schering Corporation, Kenilworth, N.J.

[21] Appl. No.: 576,319

[22] Filed: Aug. 31, 1990

Related U.S. Application Data

[60] Division of Ser. No. 307,646, Feb. 7, 1989, Pat. No. 4,988,705, which is a division of Ser. No. 17,027, Feb. 17, 1987, Pat. No. 4,810,708, which is a continuation-in-part of Ser. No. 861,788, May 15, 1986, abandoned, which is a continuation-in-part of Ser. No. 744,865, Jun. 13, 1985, abandoned.

[51] Int. Cl.$^6$ .................. A61K 31/38; A61K 31/395; C07D 471/04; C07D 239/04

[52] U.S. Cl. .................. 514/293; 514/242; 514/253; 514/254; 514/269; 514/272; 514/273; 514/274; 514/285; 514/287; 514/292; 546/81; 546/82; 546/83; 546/84; 546/64; 546/70; 544/182; 544/238; 544/246; 544/247; 544/249; 544/250; 544/405

[58] Field of Search .................. 546/81, 82, 83, 84, 546/64, 70; 514/285, 287, 292, 293, 242, 253, 254, 269, 272, 273, 274; 544/182, 238, 246, 247, 249, 250, 405

[56] References Cited

U.S. PATENT DOCUMENTS

| | | | |
|---|---|---|---|
| 3,931,199 | 1/1976 | Nakanishi et al. | 546/83 |
| 3,931,205 | 1/1976 | Nakanishi et al. | 546/83 |
| 3,947,449 | 3/1976 | Dürchkheimer et al. | 546/83 |
| 4,596,809 | 6/1986 | Sherlock | 546/84 |
| 4,680,297 | 7/1987 | Blythin et al. | 514/293 |

(List continued on next page.)

FOREIGN PATENT DOCUMENTS

| | | |
|---|---|---|
| 0127135 | 12/1984 | European Pat. Off. |
| 1585099 | 1/1970 | France |
| 2337474 | 2/1975 | Germany |
| 2803541 | 8/1979 | Germany |
| 8214590 | 1/1982 | Japan |

OTHER PUBLICATIONS

Fournier et al., *Bulletin De La Societe Chimique De France*, 1968, No. 1, pp. 364–369.
Chem. Ab. vol. 96: NO. 217821K.
Hawkins, et al., *Chem. Soc. Perkins Tans. I.* 1983, pp. 2077–2087.
Chem. Ab. vol. 85, No. 108567: p. 455 (1976).
Chemical Abstracts, vol. 101, Abstract No. 38382t, 1984.
Chem. Abstracts, 91(5): 32785e (1979) pp. 33.
Bernath, et al., *J. Heterocycl. Chem.*, 16(1), 137–44 (1979).
Chem. Abstracts, 88(13): 89668m (1978) pp. 522.
Chem. Abstracts, (85)3: 21376x (1976) pp. 695.
Chem. Abstracts, 74(15): 74797q (1971) pp. 303.
Chem. Abstracts, 85(7): 46621m (1976) pp. 536.
Chem. Abstracts, 90(25): 203821z (1979) pp. 600–601.
Chem. Abstracts, 93(5): 46364v (1980) pp. 902.
Chem. Abstracts, 95(13): 115339w (1981) pp. 686.

(List continued on next page.)

*Primary Examiner*—Johann Richter
*Attorney, Agent, or Firm*—James R. Nelson; John H. C. Blasdale

[57] ABSTRACT

Novel polycyclic quinoline, naphthyridine and pyrazinopyridine derivatives are disclosed which are useful for treating allergic reactions, inflammation, peptic ulcers, hypertension, and hyperproliferative skin diseases and for suppressing the immune response in mammals. Methods for preparing said compounds are also disclosed.

11 Claims, No Drawings

U.S. PATENT DOCUMENTS

| | | | |
|---|---|---|---|
| 4,680,298 | 7/1987 | Blythin | 514/293 |
| 4,687,774 | 8/1987 | Smith et al. | 514/293 |
| 4,760,073 | 7/1988 | Blythin et al. | 514/293 |
| 4,801,589 | 1/1989 | Smith et al. | 514/291 |
| 4,882,332 | 11/1989 | Siegel et al. | 514/255 |

OTHER PUBLICATIONS

Chem. Abstracts, 80(19): 108503g (1974) pp. 419.
Chem. Abstracts, 82(1): 4230r (1976) pp. 367–368.
Chem. Abstracts, 88(19): 130847j (1978) pp. 32.
Chem. Abstracts, 93(19): 186323f (1980) pp. 863.
Chem. Abstracts, 88(3): 22701y (1978) pp. 617.
Chem. Abstracts, 87(17): 127017n (1977) pp. 28.
Chem. Abstracts, 84(9): 59429j (1976) pp. 522.
Chem. Abstracts, 67(9): 43655t (1967) pp. 428–431.
Chem. Abstracts, 97(11): 92173n (1982) pp. 761.
Chem. Abstracts, 86(7): 43594q (1977) pp. 536.
Chem. Abstracts, 91(15): 123609s (1979) pp. 588.
Chem. Abstracts, 98:215861n (1983) pp. 584.
Chem. Abstracts, 69: 67264q (1968) 6280–6281.
Khim-Farm zh. 10(5) pp. 18–22 (1976).
Chem. Ab. 70 (1969) No. 77902y pp. 348–349.
Zh. Obshch. Khim. 38(9) pp. 2051–2064 (1968).
Australian J. Chem. vol. 27 pp. 1295–1308 D. J. Gale.
Liebigs Annalen der Chemie (1984) F. Eiden pp. 1759–1777.
Chem. Abstracts, 91(5): 32785e (1979) p. 33.

POLYCYCLIC QUINOLINE, NAPHTHYRIDINE AND PYRAZINOPYRIDINE DERIVATIVES

This is a division of U.S. Application Ser. No. 307,646 filed Feb. 7, 1989, now U.S. Pat. No. 4,988,705 which is a division of U.S. Application Ser. No. 017,027 filed Feb. 17, 1987 (now U.S. Pat. No. 4,810,708), which is a continuation-in-part of U.S. application Ser. No. 861,788 filed May 15, 1986 (now abandoned), which in turn is a continuation-in-part of U.S. Application Ser. No. 744,865 filed Jun. 13, 1985 (now abandoned).

BACKGROUND OF THE INVENTION

The present invention relates to novel polycyclic compounds which are useful in the treatment of allergic diseases, inflammation, peptic ulcers, hypertension, hyperproliferative skin diseases and in suppressing the immune response.

SUMMARY OF THE INVENTION

The invention in its chemical compound aspect involves a compound having the structural formula I

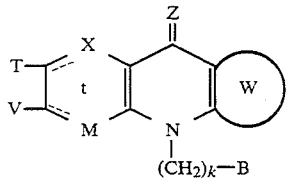

I or a pharmaceutically acceptable salt or solvate thereof, wherein:
in formula I:
the dotted lines (—) represent optional double bonds;
W is

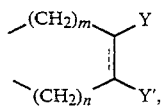

II

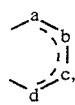

III

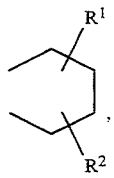

IV

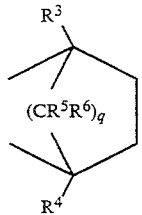

V

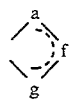

VI

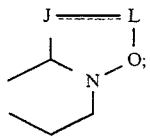

VII

T and V may be the same or different and each represents H, OH, alkyl, alkoxy, phenyl or substituted phenyl;
in addition, T may also be F, Cl, or Br;
X and M may be the same or different and each independently represents —CH($R^a$)— or —NA— when the dotted line — attached thereto does not represent a double bond; or X and M each independently represents =CH— or =N— when the dotted line — attached thereto represents a double bond; or when M is N and the dotted lines — in ring t both represent double bonds, X and T together with the carbon atom of the ring t therebetween may also represent a group

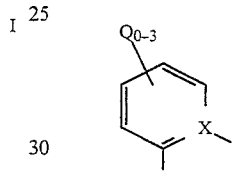

wherein X is a carbon atom and $Q_{0-3}$ represents zero, 1, 2 or 3 Q substituents as defined below;
each A is independently selected from H, alkyl, $CH_2CH_2OH$, $COR^b$, $COOR^e$, $SO_2R^b$ or $(CH_2)_sR^c$;
Z is O, S, N—$R^e$ or N(O$R^i$);
B is alkyl, alkenyl [provided k is not zero], $NH_2$, $COOR^e$, O(CO)$R^e$, or an aryl group selected from phenyl, naphthyl, indenyl, indanyl, phenanthridinyl, pyridinyl, pyrimidinyl, pyrazinyl, pyridazinyl, 1,2,4-triazinyl, furanyl, thienyl, benzofuranyl, indolyl, imidazolyl, pyrazolyl, triazolyl, or thiazolyl any of which aryl groups may be substituted with up to three of any of the following substituents, Q: halogen, hydroxy, nitro, alkyl, $CH_2OH$, trifluoromethyl, cyano, N($R^f$)$_2$, cycloalkyl, alkoxy, alkonyloxy, alkenyloxy, S(O)$_r$$R^e$, NHSO$_2$$R^e$, NHSO$_2$CF$_3$, NHCOCF$_3$, SO$_2$NH$_2$, SO$_2$NHR$^e$, SO$_2$N(R$_e$)$_2$ COR$^h$, O—D—COR$^h$, or NHCOR$^d$;
$R^a$ is H, OH, alkyl, phenyl, substituted phenyl, phenylalkyl or substituted phenylalkyl;
$R^b$ is H, alkyl, phenyl, substituted phenyl, or N($R^e$)$_2$;
$R^c$ represents carboxyl or N($R^i$)$_2$;
$R^d$ represents H, alkyl, alkoxy, COR$^j$, or NHR$^k$;
each $R^e$ independently represents alkyl, phenyl, substituted phenyl, benzyl or substituted benzyl;
each $R^f$ independently represents H or alkyl;
$R^h$ represents OH, NH$_2$ or OR$^e$;
each $R^i$ independently represents H or alkyl;
$R^j$ represents OH or alkoxy;
$R^k$ represents H or alkyl;
D represents alkylene;
k is 0, 1 or 2;
r is 0, 1 or 2; and
s is 1, 2, 3, 4 or 5;
in formula II:
the dotted line — represents an optional double bond;

Y and Y' are both H or, when — represents a double bond, Y and Y' together with the carbon atoms to which they are attached may also represent a phenyl rind which may be substituted with up to 3 substituents independently selected from hydroxy, alkoxy, alkyl or halo; and m and n may be the same or different and are 0, 1, 2, 3 or 4, provided that the sum of m and n is 1, 2, 3 or 4;

in formula III:

the dotted line — represents one optional double bond or two optional non-cumulated double bonds;

one of a, b, and c is N (if the dotted line — attached thereto represents a double bond), N+O− (if the dotted line attached thereto represents a double bond), O, S(O)$_r$, N—R$^m$, or N—CO—R$^n$, or d is N (if the dotted line — attached thereto represents a double bond), —NR$^m$, or N—CO—R$^n$, and each of the other three may be the same or different and each represents CH$_2$ or CH (if the dotted line — attached thereto represents a double bond);

r is as defined above;

R$^m$ represents H, alkyl, acyl, benzyl or substituted benzyl; and

R$^n$ represents phenol, substituted phenyl, alkoxy, phenoxy, substituted phenoxy, phenylalkoxy, or substituted phenylalkoxy;

in formula IV:

R$^1$ and R$^2$ may be the same or different and each is selected from H (provided both are not H), alkyl, phenyl, substituted phenyl, hydroxy, COOR$^e$ O(CO)R$^e$, cyano, carboxyl, CONH$_2$, CON(R$^e$)$_2$, CONHR$^e$, OR$^e$; or R$^1$ and R$^2$ are attached to the same carbon atom of the ring

and together represent a carbonyl oxygen or a ketal thereof selected from

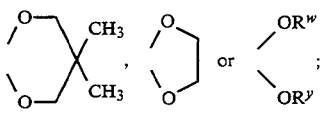

or R$^1$ and R$^2$ together with two adjacent carbon atoms of the

ring represent an epoxide, aziridine, furane, thiophene, pyrrole, N-alkylpyrrole, isopyrrole, 3-isopyrrole, pyrrolidine, triazole, triazolidine, isoxazole, isothiazole, isoxazolidine, isoxazoline, pyrazole, N-alkylpyrazole, pyrazoline, or pyrazolidine ring;

R$^w$ and R$^y$ may be the same or different and each represents alkyl; and

R$^e$ is as defined above;

in formula V:

R$^3$, R$^4$, R$^5$ R$^6$ and may be the same or different and are hydrogen or alkyl; and q is 1 or 2;

in formula VI:

the dotted line represents an optional double bond between e and f or between f and g as defined below:

e, f and g are defined as follows:

(i) e represents O, S (O)$_r$, N—R$^m$ or N—COR$^n$, and f and g both represent CR$^p$ (if the dotted line between f and g represents a double bond) or CHR$^p$; or (ii) f represents O, S(O)$_r$, N—R$^m$ or N—COR$^n$, and e and g both represent CHR$^p$; or (iii) g represents N (if the dotted line between f and g represents a double bond), f represents CR$^p$, and e represents CHR$^p$; or (iv) g represents N—R$^m$ or N—COR$^n$, and e and f both represent CR$^p$ (if the dotted line between e and f represents a double bond) or both represent CHR$^p$;

each R$^p$ is independently selected from H, alkyl, acyl or COOR$^f$; and

R$^f$, R$^m$, R$^n$ and r are as defined above; and in formula VII:

one of J and L is CHR$^q$ and the other is CR$^r$R$^s$ or, when — represents a double bond between J and L, one of J and L is CR$^q$ and the other is CR$^r$;

R$^q$ represents H, COOR$^t$, or alkyl;

R$^r$ and R$^s$ may be the same of different and each is selected from H, alkyl, acyl, —COOR$^e$, O(CO)R$^e$, —CN, phenyl sulfonyl, substituted phenyl sulfonyl, alkyl sulfonyl, nitro; or R$^q$ and R$^r$ together with the carbon atoms to which they are attached represent a carbocyclic ring having from 5 to 8 carbon atoms optionally containing one carbon-carbon double bond or represent a heterocyclic ring selected from

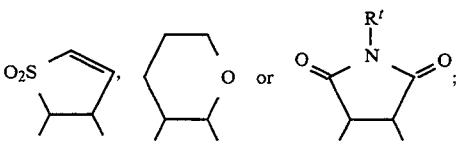

R$^e$ is as defined above; and

R$^t$ represents H, alkyl, phenyl,substituted phenyl, benzyl or substituted benzyl.

In formula I, k is preferably zero, the dotted lines in ring t preferably represent double bonds and M is preferably N. T and V are preferably H, Z is preferably O, and X is preferably CH. B in formula I is preferably phenyl or phenyl substituted with up to 3 Q substituents as defined above. Substituent Q is preferably present in the 2-, 3- or 4-; 2- and 3-; 2- and 4-; 2- and 5-; 3- and 4-; or 3- and 5-positions.

A preferred subgenus of formula II has structural formula

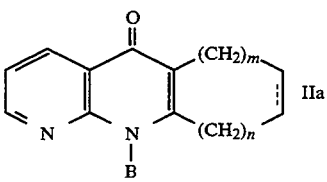

wherein B, m, and n are as defined above.

A second preferred subgenus of formula II has structural formula

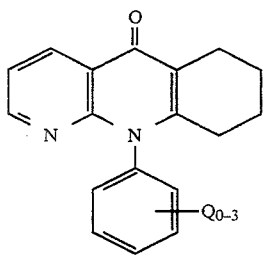

IIb wherein $Q_{0-3}$ represents up to three Q substituents as defined above. Q preferably represents a 3-Cl, 3-CH$_3$S or 3-NO$_2$ substituent in such formula.

A third preferred subgenus of formula II has structural formula

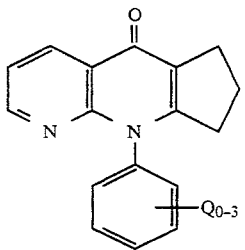

IIc wherein $Q_{0-3}$ represents up to three Q substituents as defined above. Q preferably is absent or represents a 3-CF$_3$, 3-S—CH$_3$, 4-CH$_3$ or 3-NO$_2$ phenyl substituent in a such formula.

In formula III, a, c and d preferably are CH$_2$, the dotted lines — preferably do not represent double bonds, and b preferably represents O, S(O)$_r$, or N—R$^m$ or N—CO—R$^n$ wherein r, R$^m$ and R$^n$ are as defined above. More preferably, b is N—R$^m$ and R$^m$ is acyl, e.g., acetyl.

A preferred subgenus of formula III has structural formula

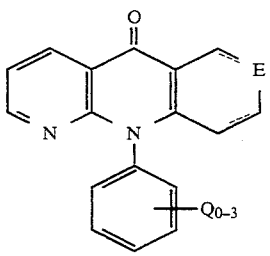

IIIa wherein the dotted lines represent optional double bonds; $Q_{0-3}$ represents up to three Q substituents as defined above; and E represents N$^+$—O$^-$ when the dotted line attached to E represents a double bond or E represents N—R$^m$ or N—CO—R$^n$ (wherein R$^m$ and R$^n$ are as defined above) when the double bond represented by the dotted line attached to E is absent.

A preferred subgenus of the compounds having ring W represented by formula is represented by the formula

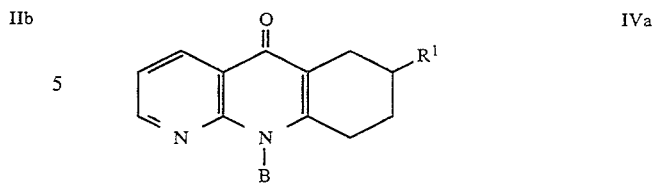

IVa wherein B and R$^1$ are as defined above. In such formula IVa, R$^1$ is preferably COOR$^e$ wherein R$^e$ is as defined above, preferably being C$_2$H$_5$ and B preferably being 3-chlorophenyl. Alternatively, R$^1$ in formula IVa is preferably CH$_3$ and B preferably represents 3-chlorophenyl, 3-methoxyphenyl, 3-methylthiophenyl or 3-nitrophenyl group.

In formula VI, e and f preferably represent CH$_2$ and the dotted lines do not represent double bonds, with g being defined as above. The letter g preferably represents N—R$^m$, more preferably N—CH$_3$ while B preferably represents phenyl or substituted phenyl such as 3-trifluoromethylphenyl.

In formula VII, the dotted line preferably does not represent a double bond and J and L together preferably represent a heterocyclic ring

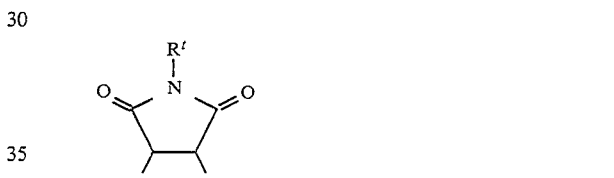

wherein R$^t$ is phenyl. Alternatively, the dotted line preferably does not represent a double bond and J and L both preferably represent CHCOOCH$_3$.

Preferred compounds of the invention include

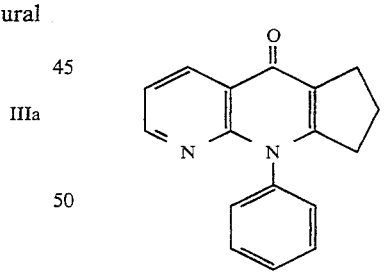

(referred to as Compound A below),

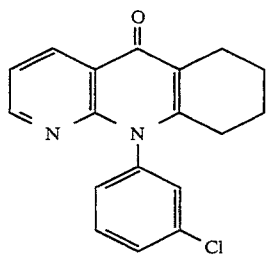

(referred to as Compound B below),

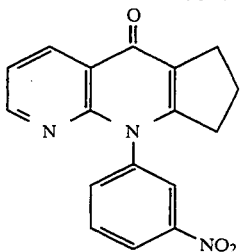

(referred to as compound C below),

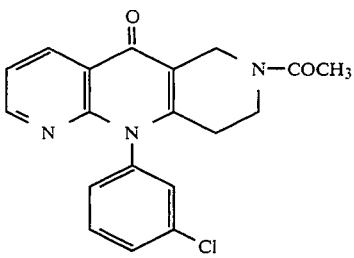

(referred to as compound D below), and

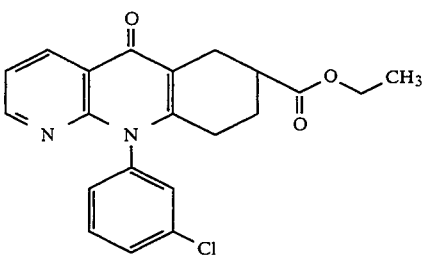

(referred to as compound E below).

or a pharmaceutically acceptable salt thereof. Compound A is particularly useful in the treatment of allergic reactions, while Compounds B, C and D are particularly useful in the treatment of inflammation.

When utilized herein, the terms below have the following scope:

halo-represents fluoro, chloro, bromo and iodo;

alkyl (including the alkyl portion of alkoxy, phenylalkyl, phenylalkoxy and alkylsulfonyl) and alkylene—represent straight and branched carbon chains and contain from 1 to 6 carbon atoms;

alkenyl—represents straight and branched carbon chains having at least one carbon to carbon double bond and contain from 2 to 6 carbon atoms;

alkenyloxy and alkynyloxy—represents straight and branched carbon chains having at least one carbon-to-carbon double or triple bond, respectively, and contains from 3 to 6 carbon atoms, with the proviso that the oxygen atom is not bound to an olefinic or acetylenic carbon atom thereof;

cycloalkyl—represents saturated carbocyclic rings having from 5 to 8 carbon atoms;

substituted phenyl, substituted phenylalkyl, substituted phenoxy, substituted phenylalkoxy, and substituted benzyl—represents phenyl, phenylalkyl, phenoxy, phenylalkoxy and benzyl groups wherein the phenyl ring thereof is substituted with up to 3 substituents Q as defined above, with the Q substituents being the same or different when there are 2 or 3 Q substituents; and acyl—represents a group alkyl—CO— wherein alkyl is as defined above.

The invention also involves a pharmaceutical composition which comprises a compound having structural formula I in combination with a pharmaceutically acceptable carrier.

The invention further involves methods for treating allergic reactions, inflammation, peptic ulcers, hypertension and hyperproliferative skin diseases (e.g., psoriasis, lichenified eczema or seborrheic dermatitis) and for suppressing the immune response in a mammal which comprises administering the above defined pharmaceutical composition to said mammal in an amount effective to achieve such purposes.

DESCRIPTION OF THE INVENTION

The group B in formula I may represent various aromatic and heterocyclic rings. These rings may be attached to the group —$(CH_2)_k$— (or to the N atom of the middle ring of structural formula I if k is zero) via any of the available substitutable atoms of such B aromatic or heterocyclic aromatic ring. Examples of suitable aryl heterocyclic groups B include 2-, 3- or 4-pyridinyl, 2- or 3-furanyl, 2- or 3-thienyl, 2, 4- or 5-thiazolyl, 2-, 4- or 5-imidazolyl, 2-, 4-, 5- or 6-pyrimidinyl, 2- or 3-pyrazinyl, 3- or 4-pyridazinyl, 3-, 5- or 6- [1,2,4-triazinyl], 2-, 3-, 4-, 5-, 6- or 7-benzofuranyl, 2-, 3-, 4-, 5-, 6- or 7-indolyl, or 3, 4- or 5-pyrazolyl.

Also, in formula IV, when $R^1$ and $R^2$ together represent a heterocyclic ring system, all possible orientations of the heteroatoms in such rings are intended. For example, and $R^1$ and $R^2$ together with the adjacent carbon atoms of the ring

to which they are attached may form a furanyl ring with the oxygen atom thereof in any possible position in the furanyl ring.

As noted above, the compounds of the invention may include up to three Q substituents on an aromatic "B" group depending upon the available sites for substitution. In compounds where there is more than one such Q substituent, they may be the same or different. Thus, compounds having combinations of different Q substituents are contemplated within the scope of the invention. Examples of suitable Q substituents include hydroxy, methyl, chloro, bromo, nitro, cyclohexyl, allyloxy, 2-propynyloxy, methylthio, methylsulfonyl, carboxy, acetoxymethoxy, acetylamino, methylsulfonylamino and the like.

Where two substituents appear on the same group, e.g. $R^e$ in $SO_2N(R^e)_2$ or $R^f$ in $N(R^f)_2$, such substituents may be the same or different. The same is true when a particular substituent (such as $R^e$) appears in two or more positions in a compound of formula I. For example, when in formula I, Z is $NR^e$, ring W is formula II, and $R^1$ represents $COOR^e$, the $R^e$ groups may be the same or different.

Certain compounds of the invention may exist in isomeric forms. The invention contemplates all such isomers both in pure form and in admixture, including racemic mixtures.

The compounds of the invention of formula I can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

Certain compounds of the invention will be acidic in nature, e.g. those compounds which possess a carboxyl or phenolic hydroxyl group. These compounds may form pharmaceutically acceptable salts. Examples of such salts are the sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain compounds of the invention also form pharmaceutically acceptable salts, e.g., acid addition salt and quaternary ammonium salts. For example, the pyrido- or pyrazino- nitrogen atoms may form salts with strong acid, while compounds having basic Q substituents such as amino groups also form salts with weaker acids. Examples of suitable acids for salt formation are hydrochloric, sulfuric, phosphoric, acetic, citric, oxalic, malonic, salicyclic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The quaternary ammonium salts are prepared by conventional methods, e.g., by reaction of a tertiary amino group in a compound of formula I with a quaternizing compound such as an alkyl iodide, etc. The free base forms differ from their respective salt forms somewhat in certain physical properties, such as solubility in polar solvents, but the salts are otherwise equivalent to their respective free base forms for purposes of the invention.

The compounds of the invention which possess an aromatic ring nitrogen atom, as defined above, may also form quaternary salts at an aromatic ring nitrogen atom.

All such acid, base and quaternary salts are intended to be pharmaceutically acceptable salts within the scope of the invention and all acid and base salts are considered equivalent to the free forms of the corresponding compounds for purposes of the invention.

The following processes A. to D. may be employed to produce various compounds in accordance with formula I. Processes A. to C. produce compounds of formula I where ring W is in accordance with formulas II, III, IV, V and VI, Z is O, and the dotted lines in ring t represent double bonds:

A. A compound of formula X

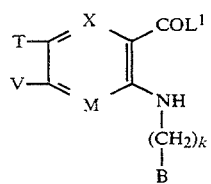

is reacted with a compound of formula XI

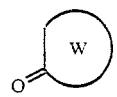

wherein M, T, V, X, k, and B are as previously defined, ring W is in accordance with formulas II to VI, and $L^1$ is a leaving group to produce a compound of formula I, a compound of formula Ia,

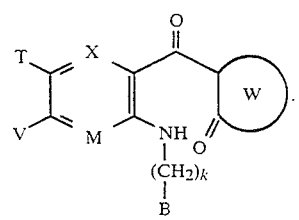

or a mixture of compounds of formulas I and Ia, and only a compound of formula Ia is produced, followed by converting the compound of formula Ia to a compound of formula I by treatment of the compound of formula Ia with strong acid; or if a mixture of compounds of formulas I and Ia was produced, optionally followed by treatment of the mixture with strong acid to convert the compound of formula Ia to a compound of formula I.

The starting materials having structural formula X and XI are known in the art. $L^1$ can be, for example, phenoxy, alkoxy, phenylalkoxy, etc. Compounds in accordance with formula X having —OH in the position of $L^1$ can be converted to compounds wherein $L^1$ is phenoxy, alkoxy or phenylalkoxy, by standard methods. Compounds of formula X wherein X and M are N, i.e., 2-substituted amino-3-pyrazine carboxylate esters may be prepared by known methods. For example, 2-phenylamino-3-pyrazine carboxylic acid is known from C.A., 75 20154e (1971).

The ketones XI, may be prepared by standard procedures or by obvious variations thereof. Other ketones having structural formula XI such as cyclopentanone, cyclohexanone and the like are available commercially.

The reaction of the compounds of formulas X and XI may be carried out by contacting X and XI in a non-reactive solvent in the presence of a basic reagent, preferably at an elevated temperature for a sufficient amount of time until the reaction is substantially completed. The progress of the reaction may be monitored by thin layer chromatography, if desired. Suitable non-reactive solvents for purposes of the reaction are tetrahydrofuran, toluene, dimethylsulfoxide, N,N-dimethylformamide and the like. Suitable basic reagents are lithium bistrimethylsilylamide, sodium amide and the like. Other suitable basic reagents and solvents will suggest themselves to those skilled in the art.

The reaction of X and XI may yield compounds of formula I, compounds of formula Ia, or a mixture of the two. If only a compound of formula Ia is formed, it may be converted to a compound of formula I by treatment with a strong acid such as p-toluenesulfonic acid in boiling toluene. Other strong acids such as sulfuric acid, aqueous hydrobromic acid, etc. may be used.

B. A compound of formula XII

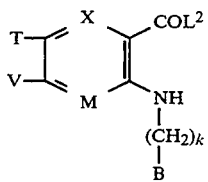

is reacted with a compound of formula XIII

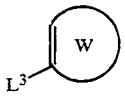

XIII wherein M, T, V, X, k, and B are as previously defined, ring W is in accordance with formulas II to VI, $L^2$ is a leaving group and $L^3$ is a leaving group (which also acts as an activating group in formula XIII), to produce a compound of formula I, a compound of formula Ib

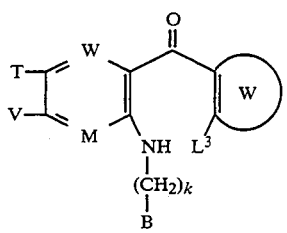

Ib or a mixture of compounds of formulas I and Ib, and if only a compound of formula Ib is produced, followed by converting the compound of formula Ib to a compound of formula I by treatment of the compound of formula Ib with strong acid, or if a mixture of compounds of formulas I and Ib was produced, optionally followed by treatment of the mixture with strong acid to convert the compound of formula Ib to a compound of formula I.

Compounds of formula XII are known or may be prepared by known methods. The choice of leaving groups $L^2$ is not critical. $L^2$ may, for example, be Cl, Br or $-OSO_2R$, wherein R is phenyl, alkyl, $-CF_3$, etc. For example, known compounds of the formula

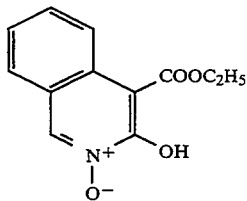

XIIa may be converted to compounds of the formula

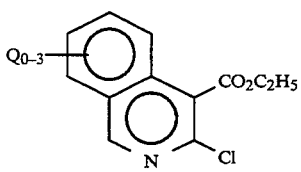

XIIb for example, by reaction with $SOCl_2$ or $POCl_3$ or $PCl_5$ to produce compounds of formula XIIb. Compounds of formula XIIb are reacted with an appropriate Primary amine, the ester group is then hydrolyzed off with, for example, base, and then the resulting compound is reacted to form the acid chloride, e.g. with thionyl chloride. For example, the following reaction scheme illustrates this process:

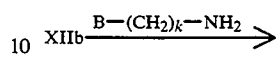

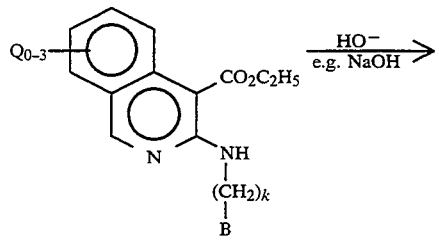

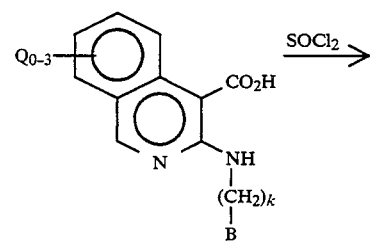

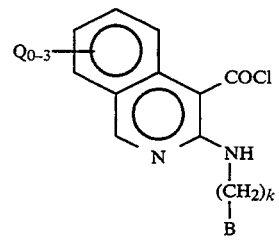

the last compound being
a compound of formula XXI.

$L^3$ is a leaving group, preferably a tertiary amino leaving group, e.g., of the formula

wherein $R^u$ and $R^v$ are alkyl, arylalkyl, heteroarylalkyl, or $R^u$ and $R^v$, together with the nitrogen atom to which they are attached may form a 5 to 8 membered saturated ring, e.g., pyrrolidine, piperidine, or morpholine. Many enamine compounds of formula XIII are known. Others may be made by known procedures, e.g., *J. Am. Chem. Soc.* 76, 2029 (1954). $L^3$ may also be, for example, $SCH_3$, e.g. from the enamine 1-methyl-2-methylmercapto-2-pyrroline.

The reaction of compounds of formulas XII and XIII is carried out in solvent, e.g., dichloromethane, benzene, toluene, etc., at temperatures ranging from $-10°$ C. to the boiling point of the solvent. The reaction proceeds in the presence of at least 2 moles of tertiary amine base, of which one mole must be of compound formula XIII. The additional base can be extra compound XIII or a different base such as, for example, triethylamine, diisopropylethylamine, etc.

The reaction of XII and XIII may yield compounds of formula I, formula Ib, or a mixture of the two. If only a compound of formula Ib is formed, it may be converted to a compound of formula I by treatment with a strong acid such as p-toluene-sulfonic acid in boiling toluene. Other strong acids, such as sulfuric acid, aqueous hydrobromic acid, etc., may be used.

C. A compound of formula XIV

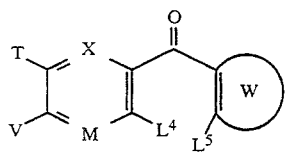   XIV is reacted with a compound of formula XV

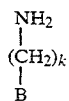   XV wherein M, T, V, X, k, and B are a previously defined, ring W is in accordance with formulas II to VI, $L^4$ is a leaving group and $L^5$ is a leaving group, to produce a compound of formula I, a compound of formula Ic

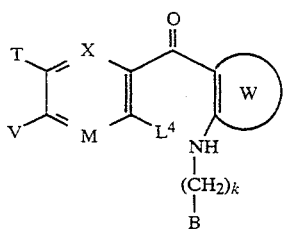   Ic or a mixture of compounds of formulas I and Ic, and if only a compound of formula Ic is produced, followed by converting the compound of formula Ic to a compound of formula I by treatment with non-nucleophilic strong acid, or if a mixture of compounds of formulas I and Ic was produced, optionally followed by treatment of the mixture with non-nucleophilic strong acid to convert the compound of formula Ic to a compound of formula I.

Compounds of formula XIV may be made by the following reaction:

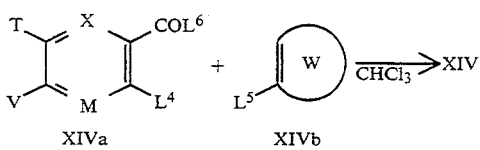

In formula XIVa, $L^6$ and $L^4$ are leaving groups such as Cl, Br, alkoxycarbonyloxy, phenoxy, benzyloxy, trifluoromethoxy, etc.

In formulas XIVb, $L^5$ is the same as $L^3$ from formula XIII. The reaction of compounds XIVa and XIVb takes place in solvent, e.g., $CH_2Cl_2$, $CHCl_3$, $CCl_4$, benzene, toluene, etc., at $-10°$ C. to about 25° C., preferably at about 0° C. This reaction like process B described above requires at least 2 moles of base of which one mole must be a compound of formula XIVb.

The primary amines of formula XV are well known and commercially available or can be made by conventional means.

The reaction of compounds XIV and XV takes place in solvent, e.g., benzene, toluene, xylene, etc. at elevated temperatures up to the boiling point of the solvent. Alternatively, the reaction can be carried out in the solvent and 1 equivalent of a strong, non-nucleophilic, preferably anhydrous acid such as p-toluenesulfonic acid, trifluoromethanesulfonic acid, etc.

The reaction of compounds XIV and XV may yield compounds of formula I, formula Ic, or a mixture of the two. If only a compound of formula Ic is formed, it may be converted to a compound of formula I by treatment with a non-nucleophilic strong acid, preferably an anhydrous acid. Preferred acids for this purpose are p-toluenesulfonic acid and trifluoromethanesulfonic acid. Of course others may be used. The reaction takes place in solvent, e.g. benzene, toluene, $CH_2Cl_2$, etc. at elevated temperatures, preferably the boiling point of the solvent. Of course, this step may be omitted if the reaction of compounds XIV and XV is carried out in presence of the acid.

D. To produce a compound of formula I wherein Z is O, the dotted lines in ring t represent double bonds, and W is

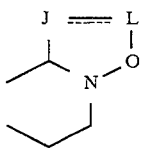   VII wherein J and L and the dotted line are as previously defined, a compound of formula XXI

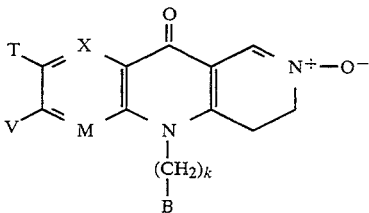   XXI wherein M, T, V, X, k, and B are as previously defined, is reacted with a compound having the formula XXIIa or XXIIb

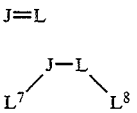

XXIIa

XXIIb to form compounds of formula I wherein W is of formula VII and the dotted line in formula VII represents a single bond, or with a compound of formula XXIIc

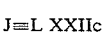  XXIIc to form compounds of formula I wherein W is of formula VII and the dotted line in formula VII represents a double bond. In formula XXIIb, $L^7$ and $L^8$ are leaving groups, e.g., halo, preferably bromo.

Compounds of formula XXIIa, XXIIb and XXIIc are well known or can be prepared by conventional methods. A process for making compounds in accordance with formula XXI is described later.

The reaction of compounds XXI with XXIIa, XXIIb, or XXIIc takes place in solvent, for example, ethyl acetate, benzene, CHCl$_3$, at elevated temperatures, preferably the boiling point of the solvent. If a compound of formula XXIIb is employed, the reaction should take place in the presence of a base such as pyridine.

In the above processes, especially in processes A, B, and C, it is desirable and sometimes necessary to protect the groups in column 1 of the following table. Conventional protecting groups are operable. Preferred protecting groups appear in column 2 of the table.

| 1. Group to be Protected | 2. Protected Group |
|---|---|
| —COOH | —COOalkyl, —COObenzyl, —COOphenyl |
| \NH/ | \NCOalkyl/, \NCObenzyl/, \NCOphenyl/ |
| \CO/ | (cyclic acetals) |
| —OH | —O-(tetrahydropyranyl) |
| —NHR, wherein R is any substituent on an amino group allowed by the claims | —N(R)-(tetrahydropyranyl), —NHCOCH$_3$, —NRCH$_2$-phenyl |
| —NH$_2$ | —N(succinimido) |

Of course other protecting groups well known in the art may be used. After the reaction or reactions, the protecting Groups may be removed by standard procedures well known in the art.

Compounds of formula I produced by processes A, B, C, or D may be converted to other compounds of formula I or to solvates or pharmaceutically acceptable salts by standard techniques. Examples of such conversions follow.

To make a compound of formula I wherein Z is O, the dotted lines in ring t represent double bonds and W is

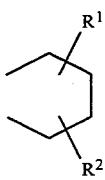

III wherein R$^1$ and R$^2$ together with two adjacent carbon atoms on the ring represent aziridine, a compound of formula XVI

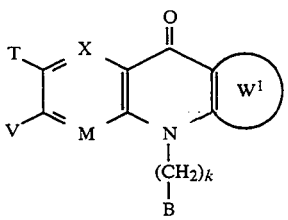

XVI wherein M, T, V, X, k, and B are as previously defined and W$^1$

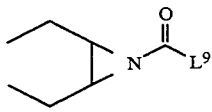

or

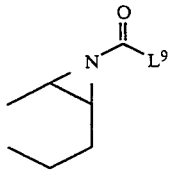

or

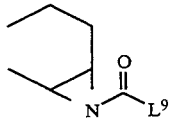

wherein L$^9$ is alkyl or alkoxy, is reacted with alkali metal hydroxide to produce a compound of formula XVII

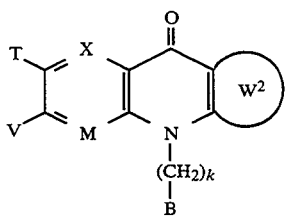

XVII wherein W$^2$ is

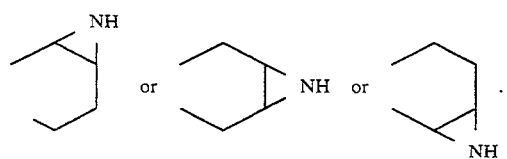

The reaction is carried out in solvent, e.g., ethanol-water.

Compounds of formula XVI are produced by the following reaction sequence

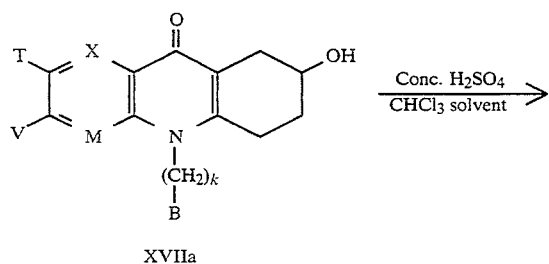

XVIIa

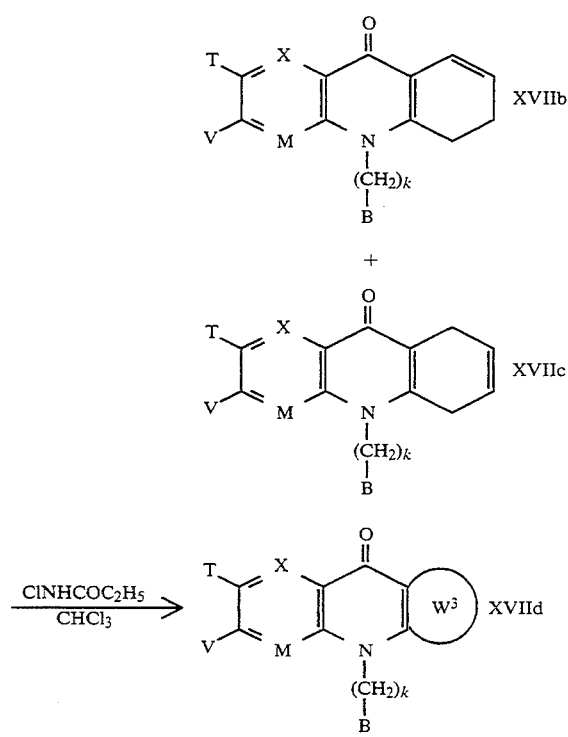

wherein $W^3$ is

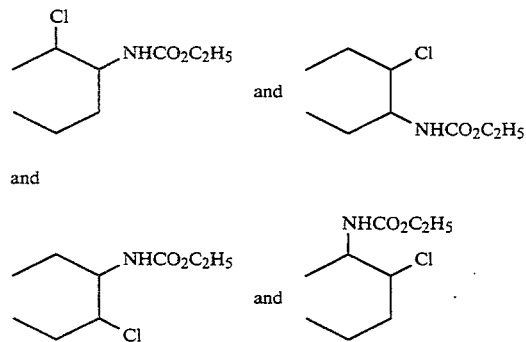

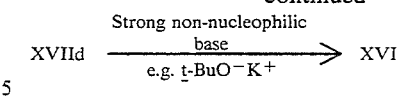

Other suitable bases that may be used in the last step are NaH and lithium diisopropylamide. The reaction may be carried out in a non-nucleophilic aprotic solvent such as tetrahydrofuran or benzene. Since a mixture of compounds in accordance with formula XVII is produced, pure compounds may be isolated if desired by using standard techniques.

To make compounds of formula XVII, wherein $W^2$ is

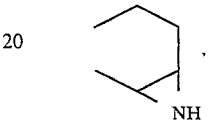

the position of the hydroxyl on formula XVIIa is shifted by standard techniques so that the starting compound has the formula XVIIe

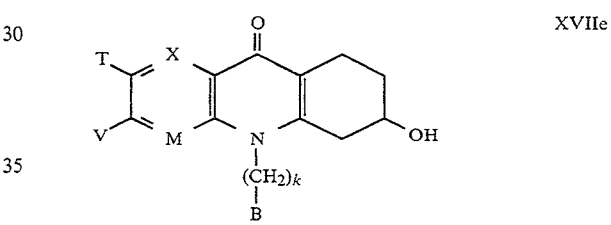

The above described reaction sequence is then followed.

To produce a compound of formula I wherein Z is O, the dotted lines in ring t represent double bonds, and W is

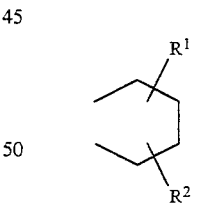

wherein $R^1$ and $R^2$ together with two adjacent carbon atoms on the ring represent an epoxide ring, a compound of formula XVIII

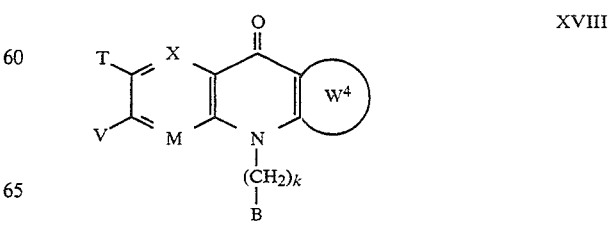

wherein $W^4$ is

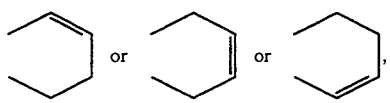

is reacted with a per acid to produce a compound of formula XIX

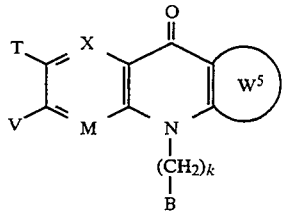

XIX wherein $W^5$ is

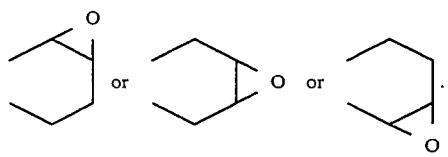

The production of compounds of formula XVIII has been described in the previous process.

Per acids that may be reacted with compounds of formula XVIII include, for example, meta-chloroperbenzoic acid, peracetic acid, and trifluoroperacetic acid. The reaction takes place at 0° C. to room temperature in solvents such as $CHCl_3$, $CH_2Cl_2$, etc.

To produce a compound of formula I wherein Z is O, the dotted lines in ring t represent double bonds, and W is

wherein E is $N^+$—$O^-$, a compound of formula XX

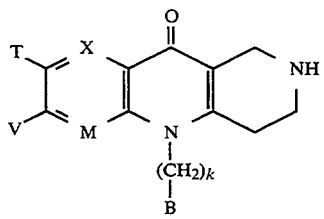

XX is reacted with $H_2O_2$ in the presence of sodium tungstate catalyst.

Compounds of formula XX may be made by processes A, B, or C. The reaction of compound XX with $H_2O_2$ takes place in water, as solvent, in the presence of sodium tungstate catalyst at 0° to 25° C.

To make a compound of formula I wherein the dotted lines in ring t are not double bonds and wherein M and X are the same or different and are $CH(R^a)$ or NH, i.e., as in formula XXV below, a compound of formula XXIV

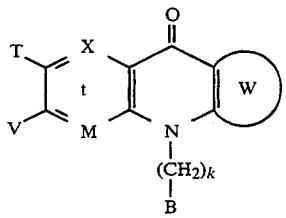

XXIV (wherein X and M are the same or different and are $C(R^a)$ or N and wherein B, k and W are as previously defined) is hydrogenated to form a compound of formula XXV

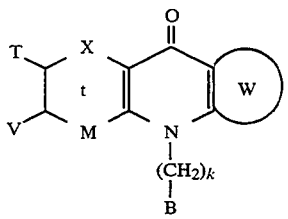

XXV

The reaction with hydrogen Gas may be carried out over 10% Pd/C catalyst in glacial acetic acid or other suitable solvent at about room temperature. The pressure may range from 1 to 4 atmospheres or higher. The temperature may range from room temperature to 100° C. or higher.

To form a compound of formula I wherein at least one of M and X represents N(A) wherein A is as defined previously but other than hydrogen, and the dotted lines in ring t are not double bonds, a compound of formula XXV

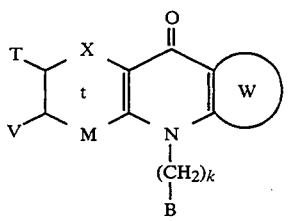

XXV wherein at least one of M and X is NH and W is as defined previously, is reacted with a compound of formula XXVI $L^{10}A^1$ XXVI wherein $L^{10}$ is a leaving group and $A^1$ is a radical in accordance with the previous definitions of A, but other than hydrogen.

In formula XXVI, if $A^1$ is alkyl, $L^{10}$ may be iodine, chlorine, bromine, etc. The reaction of XXV with XXVI requires a base, e.g., NaH, and a solvent, e.g., dimethylformamide. The temperature can range from 0° to 50° C., If $A^1$ is other than alkyl, $L^{10}$ is preferably chlorine or bromine, the solvent is toluene, $CH_2Cl_2$ or benzene, and the base is pyridine or triethylamine. The temperature may be 0° to 50° C.

To make a compound of formula I wherein Z is S a compound of formula I wherein Z is O is reacted with P₂S₅ or Lawesson's reagent, or other reagent capable of introducing sulfur in place of oxygen.

The reaction may take place at elevated temperature in pyridine or other suitable solvent. Lawesson's reagent has the formula

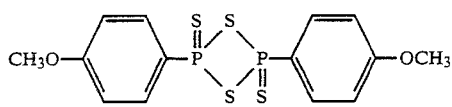

Numerous conversions of a compound of formula to another compound of formula I are possible. Many of the examples illustrate such conversions.

Compounds wherein Z represents $NR^e$ or $N(OR^j)$ may be prepared by reacting the compounds wherein Z is oxygen first with an oxaphile such as $SOCl_2$, $POCl_3$, $PCl_5$, etc., and then with the appropriate amine or hydroxylamine.

The compounds of this invention can be used to treat allergies and their preferred use is for treating allergic chronic obstructive lung diseases. Chronic obstructive lung disease as used herein means disease conditions in which the passage of air through the lungs is obstructed or diminished such as is the case in asthma, bronchitis and the like.

The anti-allergy method of this invention is identified by tests which measure a compound's inhibition of anaphylactic bronchospasm in sensitized guinea pigs having antigen-induced SRS-A mediated bronchoconstriction. Allergic bronchospasm was measured in actively sensitized guinea pigs by a modification of the procedure of Konzett and Rossler, *Arch. Exptl. Pathol. Pharmakol.*, 194, pp. 71–74 (1940). Male Hartley guinea pigs were sensitized with 5 mg ovalbumin injected ip and 5 mg injected sc in 1 ml saline on day 1 and 5 mg ovalbumin injected ip on day 4. The sensitized animals were used 3–4 weeks later. To measure anaphylactic bronchospasm, sensitized guinea pigs were fasted overnight and the following morning were anesthetized with 0.9 ml/kg ip of dialurethane. The trachea and jugular vein were cannulated and the animals were ventilated by a Harvard rodent respirator. A side arm to the tracheal cannula was connected to a Harvard pressure transducer to obtain a continuous measure of intratracheal pressure. An increase in intratracheal pressure was taken as a measure of bronchoconstriction. Each guinea pig was injected iv with 1 mg/kg propranolol, 5 mg/kg indomethacin and 2 mg/kg mepyramine given together in a volume of 1 ml/kg. Fifteen minutes later, the animals were challenged with antigen (0.5 per cent ovalbumin) delivered as an aerosol generated from a DeVilbiss Model 65 ultrasonic nebulizer and delivered through the tracheal cannula for 30 seconds. Bronchoconstriction was measured as the peak increase in intratracheal pressure occurring within 15 minutes after antigen challenge. For example, the compound 10-(3-chlorophenyl)-6,7,8,9-tetrahydrobenzo[b][1,8]-naphthyridin-5(10H)-one (Compound B), was found to inhibit anaphylactic bronchospasms in such test procedure when given at an oral dose of 0.2 mg/kg. Said compound was also found to inhibit allergen-induced SRS-A and histamine release from sensitized guinea pig lung tissue.

The compounds are effective non-adrenergic, non-anticholinergic antianaphylactic agents. The compounds may be administered by any conventional mode of administration for treatment of allergic reactions employing an effective amount of a compound of formula I for such mode. For example, when administered orally they are active at doses from about 0.2 to 10 mg/kg of body weight; when administered parenterally, e.g., intravenously, the compounds are active at dosages of from about 0.1 to 5 mg/kg body weight; when administered by inhalation (aerosol or nebulizer) the compounds are active at dosages of about 0.1 to 10 mg per puff, one to four puffs may be taken every 4 hours.

The compounds of this invention are also useful for the treatment of inflammation; thus, they are useful for the treatment of: arthritis, bursiris, tendonitis, gout and other inflammatory conditions. The anti-inflammatory use of the compounds of the present invention may be demonstrated by the Reversed Passive Arthus Reaction (RPAR)-PAW technique as set forth below using male Lewis rats (obtained from Charles River Breeding Laboratories) weighing 180–220 grams. The potency of the compounds is determined using indomethacin as the standard. On the basis of the test results, an oral dosage range of about 5 milligrams per kilogram of body weight per day to about 50 milligrams per kilogram of body weight per day in divided doses taken at about 4 hour intervals is recommended, again with any of the conventional modes of administration for treatment of inflammation being suitable.

The dosage to be administered and the route of administration depends upon the particular compound used, the age and general health of the patient and the severity of the inflammatory condition. Thus, the dose ultimately decided upon must be left to the judgment of a trained physician. The anti-inflammatory activity may be demonstrated by the following test procedures:

Reversed Passive Arthus Reaction (RPAR)

Animals, Materials and Methods

Male Lewis inbred albino rats weighing 180–220 grams obtained from Charles River Breeding Laboratories are used in these experiments. The rats are housed 3 animals/cage and food and water are allowed ad libitum. The animals are numbered 1–3 in each cage and color marked for identification purposes.

All reagents and drugs are prepared just prior to the study. Crystallized and lyophilized bovine serum albumin (BSA), obtained from Sigma Chemical Company, is solubilized without shaking in cold sterile pyrogen free saline (10 mg/ml). Lyophilized anti-bovine serum albumin (IgG Fraction), obtained from Cappel Laboratories, is suspended in sterile distilled water and diluted with cold pyrogen free saline (PFS) just prior to use. The final concentration of anti-bovine serum albumin is 0.5 mg/ml of PFS. Both BSA and anti-BSA solutions are iced during use. Drugs are suspended or solubilized in an aqueous solution of methyl cellulose (MC) with a homogenizer just prior to administration.

Groups of animals (6/group) are dosed with drug in MC by garage one hour prior to sensitization with BSA. Controls are given MC alone and drug-standard is usually included in each assay for verification purposes. Drugs are prepared so as to provide a dose for a 200 gram animal which is equivalent to the mg/kg dose for the experiment. Thus each rat receives an oral dose in a volume of approximately 2.0 cc. One hour after dosing the animals are lightly anesthetized with ether and sensitized by injecting into the penile vein 0.2 ml of PFS containing 1.0 mg of BSA. One hour later they are injected in the plantar region of one hind paw with 0.1 ml of PFS containing 0.1 mg of the anti-bovine serum albumin. Immediately after the subplantar injection, the injected paw is dipped (up to the lateral maleolus) into the mercury well of a plethysmograph. The volume of mercury displaced is converted to weight and recorded. This value is considered to be the control paw volume for the animal. Paw volumes are also recorded with a plethysmograph during the development of the inflammation at 2 and 4 hours post-challenge. Compounds B, C and D provided $ED_{50}$ values of about 0.4, 0.1 and 0.4 mg/kg, respectivley, p.o. in this procedure.

Another procedure for testing for acute anti-inflammatory activity measures the reverse passive Arthus reaction in the pleural cavity of rats as described in Myers et al, *Inflammation,* Vol. 9, No. 1, 1985, pp. 91–98. Compounds B and C provide $ED_{50}$ values of about 0.4 mg/kg and 0.1 mg/kg, respectively, p.o. in such procedure.

The compounds of this invention are also useful in the treatment of peptic ulcers. They display chemotherapeutic activity which enables them to relieve the symptoms of peptic ulcer disease, stress ulceration, and promote healing of gastric and/or duodenal ulcers. The compounds are also useful as conjunctive therapeutic agents for coadministration with such anti-inflammatory/analgesic agents as aspirin, indomethacin, phenylbutazone, ibuprofen, naproxen, tolmetin and other agents. The compounds of this invention prevent the untoward side effects of irritation and damage to the gastrointestinal tract caused by such agents. The anti-ulcer activity of the compounds of this invention is identified by tests which measure their cytoprotective effect in rats.

The compounds-of this invention may be evaluated for their antiulcer activity characteristics by the procedures which measure the cytoprotective effect in rats e.g., as described in Chiu et al., *Archives Internationales de Pharmacodynamie et de Therapie,* 270, 128–140 (1984). Compound A at 10 mg/kg provided an 82% inhibition of Indomethacin-induced gastric ulcers.

In the treatment of peptic ulcer disease, and the prevention and treatment of drug-induced gastric ulceration, the active compounds of this invention can be administered in conventional unit dosage forms such as tablets, capsules, pill, powders, granules, sterile parenteral solutions or suspensions, suppositories, mechanical delivery devices, e.g., transdermal, and the like. The compounds of this invention may be administered at doses of about 0.3 to about 30 mg/kg, preferably, from about 2 to about 15 mg/kg, of body weight per day. Preferably, the total dosages are administered 2–4 divided doses per day.

The compounds of the invention are also useful as antihypertensive agents in the treatment of hypertension. The compounds effectively lower blood pressure in spontaneously hypertensive rats (SHR), an animal model of human essential hypertension, without affecting the blood pressure of normotensive rats. This activity may be demonstrated by the procedure described below.

Male spontaneously hypertensive rats or normotensive Sprague-Dawley rats were-used. Blood pressure is measured according to standard procedures as described in detail in Baum T., Sybertz E. J., Watkins R. W., et al., Antihypertensive activity of SCH 31846, a non-sulfhydryl angiotensin-converting enzyme inhibitor. *J. Cardiovas. Pharmacol.* 5:655–667, 1983.

Animals are allowed at least 1.5-2 hours equilibration prior to experimentation. Test drugs are administered orally in a methylcellulose vehicle-in a volume of 2 ml/kg and blood pressure is monitor for 4 hours following dosing. Compound A above at oral dosages of 10 and 30 mg/kg, reduced blood pressure significantly by $-21\pm 4$ (mean $\pm$ SEM) and $-35\pm 4$ mm Hg, respectively, in the spontaneously hypertensive rats. In contrast, Compound A did not lower blood pressure in the normotensive Sprague Dawley rats. Compounds B and C at an oral dosage of 30 mg/kg lowered blood pressure by $-19\pm 2$ and $-24\pm 2$ mm Hg, respectively, in the SHR and caused negligible changes in blood pressure of normotensive Sprague Dawley rats.

The dosage range for the antihypertensive method of the invention may vary from about 3 to about 100 mg/kg, preferably about 10 to about 30 mg/kg per day, in divided doses if desired. The dose will be varied depending on a number of factors, including inter alia the hypertensive disease being treated, the patient, the potency of the particular compound employed, etc. The compounds of formula I can be administered by conventional modes, e.g. orally, intraveneously, etc., in any conventional form for such purpose such as solutions, capsules, tablets, pills, powders, sterile parenteral solutions or suspensions, transdermal compositions or the like.

The compounds of formula I are useful in the treatment of hyperproliferative skin disease, e.g., psoriasis, in mammals, e.g., humans, which may be demonstrated by the Arachidonic Acid Mouse Ear Test as described below.

Arachidonic Acid Mouse Far Test,

Materials and Methods

Charles River, female, CD, (SD) BR mice, 6 weeks old, are caged 8/group and allowed to acclimate 1–3 weeks prior to use.

Arachidonic acid (AA) is dissolved in reagent grade acetone (2 mg/0.01 ml) and stored at $-20°$ C. for a maximum of 1 week prior to use. Inflammatory reactions are induced by apply 10 ml of AA to both surfaces of one ear (4 gm total).

Test drugs are dissolved in either reagent grade acetone or aqueous ethanol (only if insoluble in acetone) at the same doses selected by Opas et al., *Fed. Proc.* 43, Abstract 2983, p. 1927 (1984) and Young et al., *J. Invest. Dermatol.* 82, pp. 367–371 (1984). These doses are employed to ensure maximum responses and to overcome any difference in topical absorption which could occur with any drug applied in an aqueous ethanol vehicle. The test drug is applied 30 minutes prior to challenge with AA.

The severity of the inflammation is measured as a function of increased ear weight. A 6 mm punch biopsy is removed 1 hour after AA challenge and weighed to the nearest 0.1 mg. Mean $\pm$ standard error and all possible comparisons are made via Duncan's Multiple Range Statistic.

Compounds A, B, and C provided $ED_{50}$ values of 0.15 mg, 0.07 mg, and 0.01 mg, respectively in the above test procedure.

As a result of the topical administration of a compound of formula I, a remission of the symptoms of the psoriatic patient, in most cases, can be expected. Thus, one affected by psoriasis can expect a decrease in scaling, erythema, size of the plaques, pruritus and other symptoms associated with psoriasis. The dosage of medicament and the length of time required for successfully treating each individual psoriatic patient may vary, but those skilled in the art of medicine will be able to recognize these variations and adjust the course of therapy accordingly.

Included within the invention are preparations for topical application to the skin whereby the compounds having structural formula I are effective in the treatment and control of skin diseases characterized by rapid rates of cell proliferation and/or abnormal cell proliferation, e.g., psoriasis.

In a preferred method of treating hyperproliferative skin diseases, a pharmaceutical formulation comprising a compound of formula I, (usually in concentrations in the range of from about 0.001 percent to about 10 percent, preferably from about 0.1 percent to about 5 percent) together with a non-toxic, pharmaceutically acceptable topical carrier, is applied several times daily to the affected skin until the condition has improved. Topical applications may then be continued at less frequent intervals (e.g. once a day) to control mitosis in order to prevent return of severe disease conditions.

The compounds of the invention are also useful in the treatment of autoimmune and other immunological diseases including graft rejection in which T cell proliferation is a contributing factor to the pathogenesis of disease. The effectiveness of these compounds as immunosuppressing agents may be demonstrated by the following tests which involve the inhibition of T cell functions using these compounds.

GRAFT VS. HOST REACTION (GVHR)

To induce a GVHR, C57 B1/6XA/J(F6AF1) male mice were injected intravenously with parental (C57B1/6J) spleen and lymph node cells. The compound (Compound A) was then administered orally for 10 days beginning on the day prior to the cell transfer. On the day following the last treatment, the animals were sacrificed, and their spleens were excised and weighed. The enlargement of the spleen of the host is a result of a GVHR. To some extent it is the host's own cells which infiltrate and enlarge the spleen although they do this because of the presence of graft cells reacting against the host. The amount of spleen enlargement, splenomegaly, is taken as a measure of the severity of the GVHR.

In carrying out the GVHR the animal in the experimental group is injected with parental cells, cells of the same species but of different genotype, which cause a weight increase of the spleen. The animal in the control group is injected with syngeneic cells, genetically identical cells which do not cause a weight increase of the spleen. The effectiveness of the compounds administered to the mice in the experimental group is measured by comparing the spleen weight of the untreated and treated GVH animal with that of the syngeneic control. Compound B reduced spleen weight by 12%, 29% and 100% at doses (mg/kg) of 25, 50 and 100, respectively, as compared to the untreated animals; while Compound C reduced spleen weight by 46%, 129% and 100% at doses (mg/kg) of 25, 50 and 100, respectively, compared to untreated animals.

SPLENIC ATROPHY

The immunosuppressive activity of the compounds may also be shown by a decrease in spleen weight after dosing $BDF_1$ mice orally with the drug for seven (7) consecutive days. The mice are sacrificed on the eighth day. The percent decrease in spleen weight is measured for each dosage level. In this procedure, Compound B provided a 27%, 25% and 24% spleen weight decrease at dosage levels of 25, 50 and 100 mg/kg, respectively; while Compound C provided a 31%, 35% and 33% spleen weight decrease at dosage levels of 25, 50 and 100 mg/kg, respectively.

As noted above, the subject compounds possess acute anti-allergy and anti-inflammatory activities. For example, Compounds B and C have $ED_{50}$ values of less than about 0.5 mg/kg and 5 mg/kg, respectively, p.o. in tests measuring the inhibition of anaphylactic bronchospasm in sensitized guinea pigs having antigen-induced bronchoconstriction and $ED_{50}$ values of about 0.4 mg/kg and 0.1 mg/kg, respectively, p.o. in tests measuring the reverse passive Arthus reaction in the pleural cavity of rats (as described by Myers et al., *Inflammation*, Vol. 9, No. 1, 1985, pp. 91–98). Compounds B and C have $ED_{50}$ values of Greater than about 50 mg/kg and 25 mg/kg, respectively, in the GVHR test as described above. These results for Compound B and C and similar results obtained for other compounds of formula I tested to date indicate that an immunosuppressive effective dose for such compounds is several times or more their anti-inflammatory and anti-allergy effective doses.

The usual dosage range for the immunosuppressive method of the invention with the compounds of formula I in a 70 kg mammal is an oral dose of about 0.1 to 250 mg/kg, preferably 0.1 to 150 mg/kg, in 3 or 4 divided doses per day. Of course, the dose will be regulated according to the potency of compound employed, the immunological disease being treated, and the judgment of the attending clinician depending on factors such as the degree and the severity of the disease state and age and general condition of the patient being treated.

To treat immunological diseases, the active compounds of formula I can be administered in unit dosage forms such as tablets, capsules, pills, powders, granules, sterile parenteral solutions or suspensions, suppositories, transdermal compositions and the like. Such dosage forms are prepared according to standard techniques well known in the art.

Some of the compounds of-this invention are also useful in preventing cardiac anaphylaxis.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethyl-cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For predating suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Formulations for topical application, e.g., for use in treating hyperproliferative skin diseases, may include the above liquid forms, creams, aerosols, sprays, dusts, powders, lotions and ointments which are prepared by combining an active ingredient according to this inventions with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oily base and will, in general, also include one or more of the following, namely, stabilizing agents, emulsifying agents, dispersing agents, suspending agents, thickening agents, coloring agents, perfumes and the like.

Powders may be formed with the aid of any suitable powder base, e.g., talc, lactose, starch, etc. Drops may be formulated with an aqueous base or non-aqueous base also comprising one or more dispersing agents, suspending agents, solubilizing agents, etc.

The topical pharmaceutical compositions according to the invention may also include one or more preservatives or bacteriostatic agents, e.g., methyl hydroxybenzoate, propyl hydroxybenzoate, chlorocresol, benzalkonium chlorides, etc.

The topical pharmaceutical compositions according to the invention may also contain other active ingredients such as antimicrobial agents, particularly antibiotics, anesthetics, analgesics and antipruritic agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

When administered parenterally, e.g. intravenously, the compounds are administered at a dosage range of about 1–30 mg/kg of body weight in single or multiple daily doses.

The quantity of active compound in a unit dose of preparation may be varied or adjusted from 1 mg to 100 mg according to the particular application and the potency of the active ingredient. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily; dosage may be divided and administered in portions during the day if desired.

The following examples are intended to illustrate, but not to limit, the present invention.

PREPARATIVE EXAMPLE 1

Dissolve 2-chloronicotinoyl chloride (0.10 mole) in $CHCl_3$ (90 ml). Add the resulting solution to a 5° C. solution of triethylamine (0.10 mole) and an enamine, 1-(1-pyrrolidinyl)-1-cyclopentene (0.10 mole), dissolved in $CHCl_3$ (90 ml). Allow C-acylation to proceed for 21 hrs., while the temperature of the reaction mixture rises to 25° after the second hour. Monitor the course of the reaction by thin-layer chromatography as needed. Wash the resulting solution with water,-aqueous $NaHCO_3$ solution, and with water. After drying, carefully evaporate solvent to obtain the enaminoketone, (2-chloro-3-pyridinyl)[2-(1-pyrrolidinyl)-1-cyclopenten-1-yl]methanone, m.p. 102.5°–104.0° C., after recrystallization from ethyl acetate. This compound is referred to in Examples 1 and 3 below as Compound 1.

By employing the acid chloride and enamine listed in Columns 1 and 2 of Table 1 below, the compounds listed in Column 3 are prepared. In some instances $CH_2Cl_2$ is used in place of $CHCl_3$ and the reaction time is varied. 2-Chloronicotinoyl and 2-chloro-3-pyridazinylcarbonyl chloride are available from Chemo Dynamics Inc., whereas the Aldrich Chemical Co. supplies certain enamines, e.g. 1-pyrrolidino-1-cyclopentene, 1-morpholino-1-cyclohexene, and 1-pyrrolidino-1-cyclohexene. Other enamines employed here and elsewhere in the following examples are prepared according to *J. Am. Chem. Soc.* 76, 2029 (1954) or other methods. For example, the indicated enamines may be prepared by the methods disclosed in the articles listed after each: 2-(1-pyrrolidino)-indene, *J. Org. Chem.* 26, 3761 (1961); 1-methyl-2-methylmercapto-2-pyrroline, *Org. Syn.* 62, 158 (1984) and *Liebigs Ann. Chem.* 725, 70 (1969); 4-carbethoxy-1-(1-pyrrolidino)-cyclohexene, 1,2-dicarbethoxy-4-(1-pyrrolidino)-4-pyrroline, 1-acetyl-3-( 1-pyrrolidino)-2-pyrroline, and 1-acetyl-4-(1-pyrrolidino)-1,2,5,6-tetrahydropyridine, *J. Am. Chem. Soc.* 76, 2029, (1954); and 5,6-dihydro-4-(1-pyrrolidino)-2H-thiopyran, *Zh. Organ. Khim.*, 1, 1108 (1965). The following ketone starting materials for the enamines may be prepared, for example, by the methods disclosed in the articles listed after each: 4-carbethoxycyclohexanone, *Synth. Commun.* 15, 541 (1985); 1,2-dicarbethoxy-4-pyrrolidinone, *J. Org. Chem.* 38, 3487 (1973); 1-acetyl-3-pyrrolidinone, *J. Med. Chem.* 5, 762 (1962).

TABLE 1

| Col. 1 Acid Chloride | | | Col. 2 Enamine | Col. 3. Product[1] | Col. 4 Product m.p. °C. (solvent of crystallization) |
|---|---|---|---|---|---|
| X | M | L[4] | | G = | |
| N | N | Cl | (1-pyrrolidino-1-cyclopentene) | (1-pyrrolidino-cyclopentene) | 110–112 ($CCl_4$-Pet. ether) |
| CH | CH | Br | " | " | oil |
| CH | N | Cl | (1-morpholino-1-cyclohexene) | (morpholino-cyclohexene)[2] | oil |
| CH | N | Cl | (1-pyrrolidino-4-methyl-1-cyclohexene) | (pyrrolidino-4-methyl-cyclohexene) | oil |
| CH | N | Cl | (2-(1-pyrrolidino)-dihydronaphthalene) | (pyrrolidino-dihydronaphthalene) | 168–172° ($CH_3COOC_2H_5$) |

[1] X, M and L[4] same as in column 1.
[2] Referred to as Compound 2 in Example 2 below.

PREPARATIVE EXAMPLE 2

Add equimolar amounts of ethyl glycinate hydrochloride, triethylamine, and (2-chloro-3-pyridinyl)[2-(1-pyrrolidinyl)-1-cyclopenten-1-yl]methanone to t-butyl alcohol (170 ml per 0.020 mole of amine). Reflux the resulting mixture for 34 hrs, monitoring the reaction by thin-layer chromatography as needed. Cool the reaction mixture, and evaporate solvent. Wash a CHCl$_3$ solution of the residue with water and with saturated aqueous NaCl solution. After drying the organic solution, evaporate the solvent to obtain the resulting enaminoketone, (2-chloro-3-pyridinyl) [2-(1-ethoxycarbonylinethanaminyl)-1-cyclopenten-1-yl]methanone, m.p. 114.5°–117.5° C., after recrystallization from isopropanol.

EXAMPLE 1

Dissolve the primary amine, 3-nitroaniline, and the enaminoketone (Compound 1 above) in benzene containing anhydrous p-toluenesulfonic acid. Let the molar ratio of the primary amine to enaminoketone be about 1.25 and that of acid to enaminoketone be 1. Use enough benzene to Give a solution that is initially 1M in enaminoketone. Reflux the resulting solution 26 hours, and monitor the course of the reaction by thin-layer chromatography as needed. Cool the reaction mixture, evaporate the solvent, and dissolve the residue in CHCl$_3$. Wash the CHCl$_3$ solution with water, aqueous NaHCO$_3$ solution, dilute aqueous HCl solution, and with water. After drying the CHCl$_3$ solution, evaporate solvent to obtain the resulting naphthyridinone, 9-(3-nitrophenyl)-6,7,8,9-tetrahydro-5H-cyclopenta[b][1,8]-naphthyridin-5-one, m.p. 276°–277° C., after recrystallization from CH$_3$CN.

EXAMPLE 2

Dissolve 3-chloroaniline (0.0733 mol) and the enaminoketone (Compound 2 in Table 1 above) (0.0539 mol) in benzene (50 ml) containing p-toluenesulfonic acid monohydrate (0.0523 mol). Reflux the solution for 18 hours, removing water with a Dean Stark trap. Cool the resulting mixture and evaporate the solvent, dissolving the residue in CHCl$_3$. Wash the CHCl$_3$ solution with water, 2N HCl, water, in NaHCO$_3$, and with water. Dry and filter the CHCl$_3$ solution, and evaporate the solvent to give 10-(3-chlorophenyl)-6,7,8,9-tetrahydrobenzo[b][1,8]naphthyridin-5(10H)-one, m.p. 195°–198° C. after crystallization from CH$_3$CN.

By employing the primary amine the enaminoketone as indicated in Columns 1 and 2 of Table 2 below, the naphthyridinones or pyrazinopyridones as indicated in Column 3 of Table 2 are prepared by basically the same methods as described in Examples 1 and 2.

TABLE 2

| Col. 1 Primary Amine B in NH$_2$—B | Col. 2 Enaminoketone | | | | Col. 3 Product[3] W = | Col. 4 Product m.p. °C. (solvent of crystallization) |
|---|---|---|---|---|---|---|
| | V | X | L$^4$ | G | | |
| 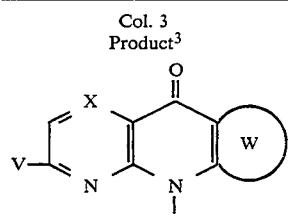 | H | CH | Cl | 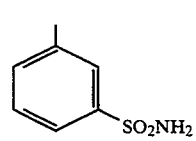 | 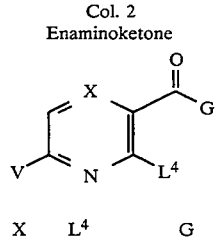 | 321–324 (CH$_3$CN) |
| 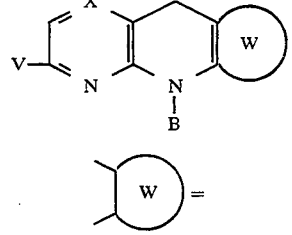 | H | CH | Cl | " | " | 306–308 (CH$_3$CN) |
| 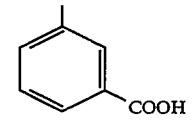 | H | CH | Cl | " | " | 230–233 (CH$_3$CN) |

TABLE 2-continued

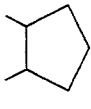

| Col. 1 Primary Amine B in NH$_2$—B | V | X | L$^4$ | G | W = | Col. 4 Product m.p. °C. (solvent of crystallization) |
|---|---|---|---|---|---|---|
| 4-Cl-3-NO$_2$-C$_6$H$_3$ | H | CH | Cl | " | " | 303–306 (CH$_3$CN) |
| 3-CN-C$_6$H$_4$ | H | CH | Cl | " | " | 287–290 (CH$_3$CN) |
| 3,4-Cl$_2$-C$_6$H$_3$ | H | CH | Cl | " | " | 294–296 (CH$_3$CN) |
| 3,5-Cl$_2$-C$_6$H$_3$ | H | CH | Cl | (pyrrolidinyl cyclopentene) | (cyclopentyl) | 270–273 (CH$_3$CN) |
| C$_2$H$_5$O(CO)CH$_2$ | * | * | * | * | " | 151–153.5 (CH$_3$CN) |
| 4-OCH$_3$-C$_6$H$_4$ | H | CH | Cl | " | " | 212–215 (CH$_3$CN) |
| 4-CH$_3$-C$_6$H$_4$ | H | CH | Cl | " | " | 242–244.5 (CH$_3$CN) |
| 3-SCH$_3$-C$_6$H$_4$ | H | CH | Cl | " | " | 210.5–213.5 (CH$_3$CN) |

TABLE 2-continued

| Col. 1 Primary Amine B in NH$_2$—B | Col. 2 Enaminoketone | | | | Col. 3 Product | Col. 4 Product m.p. °C. (solvent of crystallization) |
|---|---|---|---|---|---|---|
| | V | X | L$^4$ | G | W = | |
| 3-chlorophenyl | H | N | Cl | pyrrolidinyl-cyclopentenyl | cyclopentane-fused | 278–280 (CHCl$_3$/CH$_3$COCH$_3$) |
| 3,4-dichlorophenyl | H | N | Cl | " | " | >300 (d) (CHCl$_3$/CH$_3$COCH$_3$) |
| 3-nitrophenyl | H | N | Cl | " | " | >300 (d) (CH$_3$COCH$_3$) |
| phenyl | H | N | Cl | " | " | >300 (d) (CH$_3$COCH$_3$) |
| 3-nitrophenyl | H | CH | Cl | morpholinyl-cyclohexenyl | cyclohexane-fused | 255–259 (1,4-dioxane) |
| phenyl | H | CH | Cl | morpholinyl-cyclohexenyl | cyclohexane-fused | 256.5–260 (CH$_3$CN) |

TABLE 2-continued

| Col. 1 Primary Amine B in NH₂—B | V | X | L⁴ | G | W = | Col. 4 Product m.p. °C. (solvent of crystallization) |
|---|---|---|---|---|---|---|
| 3-chlorophenyl | H | CH | Cl | pyrrolidinyl-cyclohexenyl-CH₃ | dimethylcyclohexyl | 207–209 (CH₃CN) |
| phenyl | H | CH | Cl | " | " | 211–223 (CHCl₃/CH₃COCH₃) |
| 3-methoxyphenyl | H | CH | Cl | " | " | 185–187 (CH₃CN) |
| 3-(methylthio)phenyl | H | CH | Cl | " | " | 201–203 (CH₃COCH₃) |
| 3-(ethoxycarbonyl)phenyl | H | CH | Cl | " | " | 192–194 (CH₃CN) |
| 3-nitrophenyl | H | CH | Cl | pyrrolidinyl-cyclohexenyl-CH₃ | dimethylcyclohexyl | 230–233 (CH₃CN) |

TABLE 2-continued

| Col. 1 Primary Amine B in NH₂—B | Col. 2 Enaminoketone | | | | Col. 3 Product | Col. 4 Product m.p. °C. (solvent of crystallization) |
|---|---|---|---|---|---|---|
| | V | X | L⁴ | G | W = | |
| phenyl | H | CH | Cl | (4-pyrrolidinyl-3,4-dihydronaphthalen-2-yl) | tetrahydronaphthalene-fused | 265–267 (1,4-dioxane) |
| 3-(dimethylamino)phenyl | H | CH | Cl | 1-pyrrolidinyl-cyclopentenyl | cyclopentane-fused | 238–239.5 (CH₃CN) |
| 4-hydroxyphenyl | H | CH | Cl | " | " | >350 (DMF) |
| phenyl | H | CH | Cl | pyrrolidinyl-cyclohexenyl with dioxaspiro ketal | cyclohexane-fused with 2,2-dimethyl-1,3-dioxane spiro | 235–238.5 (CH₃COOC₂H₅/ CH₃OH) |
| phenyl | H | CH | Cl | 2-methylthio-1-methyl-4,5-dihydropyrrol-3-yl | 1-methylpyrrolidine-fused | 245.5–248 (CH₃CN) |

TABLE 2-continued

| Col. 1 Primary Amine B in NH₂—B | Col. 2 Enaminoketone | | | | Col. 3 Product | Col. 4 Product m.p. °C. (solvent of crystallization) |
|---|---|---|---|---|---|---|
| | V | X | L⁴ | G | W = | |
| 3-Cl-phenyl | H | CH | Cl | pyrrolidinyl-cyclohexenyl | 3,4-dimethyl-phenylcyclohexyl | 225–230 (eluent on silica gel column is 1% $CH_3OH$ in $CHCl_3$) |
| 4-Cl-2-CH₃-phenyl | H | CH | Cl | morpholinyl-cyclohexenyl | cyclohexyl | 201–203 ($CH_3CN$) |
| 3-Cl-phenyl | $CH_3$ | CH | Cl | pyrrolidinyl-cyclohexenyl | " | 218–220.5 ($CH_3CN$) |

[3] B same as in column 1 and X and V same as in column 2.
*Prepared using the compound of Preparative Example 2.

By employing the primary amines and enaminoketones as indicated in Columns 1 and 2 of Table 3 below, the compounds of Column 3 may also be prepared by basically the same method.

TABLE 3

| Col. 1 Primary Amine B in NH₂—B | V | X | L⁴ | Col. 2 Enaminoketone | Col. 3 Product⁴ |
|---|---|---|---|---|---|
| [pyrimidine] | H | CH | Cl | [pyrrolidinyl cyclopentene] | [cyclopentyl] |
| [pyrazine] | H | N | Cl | " | " |
| [pyrazole-NH] | H | N | Cl | " | " |
| [1,2,4-triazole-NH] | H | N | Cl | " | " |
| [methylthiazole] | H | N | Cl | " | " |

⁴B same as in column 1 and X and V same as in column 2.

EXAMPLE 3

Mix aniline and the enaminoketone (Compound 1 above) in a molar ratio of 1.25:1, and heat the mixture 51 hours at 110° C. and 24 hours at 125° C. Cool the resulting mixture, dissolve it in CHCl₃, and treat the CHCl₃ solution as described in Example 1 above to produce 9-phenyl-6,7,8,9-tetrahydro-5H-cyclopenta[b][1,8]naphthyridin-5-one, m.p. 235°–237° C., after recrystallization from CH₃CN.

By employing the primary amines and enaminoketones as indicated in Columns 1 and 2 of Table 4 below, the compounds listed in Column 3 thereof are prepared by basically the same method varying the reaction time from 4.5–100 hrs. and the temperature from 110°–130° C. as necessary. If the amine used in this example is hydrazine, then use a molar ratio of hydrazine to enaminoketone of 8.5:1.

TABLE 4

Col. 1 Primary Amine $NH_2-(CH_2)_k-B$

Col. 2 Enaminoketone

Col. 3 Product[5]

Col. 4 Product m.p. °C. (solvent of crystallization)

| k | B | X | L⁴ | G = | W = | Product m.p. °C. (solvent of crystallization) |
|---|---|---|---|---|---|---|
| 0 | NH₂ | CH | Cl | (1-pyrrolidinyl)cyclopenten-1-yl | cyclopentyl | 206–210 (d) (CH₃CN) |
| 0 | 3-chlorophenyl | CH | Cl | " | " | 261–264 (CH₃CN) |
| 1 | 4-fluorophenyl | CH | Cl | " | " | 177–178.5 (CH₃CN) |
| 0 | 3-methoxyphenyl | CH | Cl | " | " | 259.5–261 (CH₃CN) |
| 0 | 3-pyridyl | CH | Cl | " | " | 242–243 (CH₃COOC₂H₅) |

[5]B and k same as in column 1 and X same as in column 2.

EXAMPLE 4

Reflux a solution of (2-bromophenyl) [2-(1-pyrrolidinyl)-1-cyclopenten-1-yl]-methanone (14.1 g) (from Preparative Example 1) in benzene (100 ml) containing aniline (4.5 ml) and p-toluenesulfonic acid monohydrate (8.8 g) for 19 hrs. Remove water continuously with a Dean-Stark trap. Wash the cooled solution with water, 1M NaHCO₃ solution, and with water. Dry the benzene solution, filter it, and evaporate the solvent. Crystallize to obtain (2-bromophenyl)[2-(phenylamino)-1-cyclopenten-1-yl]methanone, m.p. 106-5°–108.5° from CH₃CN.

Reflux a mixture of (2-bromophenyl) [2-(phenylamino)-1-cyclopenten-1-yl]-methanone (5.8 mmol), potassium tert.-butoxide (0.71 g), and tert.-butanol (25 ml) under nitrogen for 1 hr. Monitor the ensuing reaction by thin-layer chromatography, and cool the mixture when reaction is complete. Evaporate tert.-butanol, add water (25 ml) to the residue, and filter off the product, 1,2,3,4-tetrahydro-4-phenyl-9H-cyclopenta[b]quinolin-9-one, m.p. 265–267, after crystallization from CH₃CN/CHCl₃.

PREPARATIVE EXAMPLE 3

Prepare 2-(3-chlorophenylamino)pyridinyl-3-carbonyl chloride as follows. Add excess thionyl chloride (0.6 ml per mmol of acid) to 2-(3-chlorophenylamino)pyridinyl-3-carboxylic acid (0.38 mol), and allow the resulting mixture to stand or stir at 25° C. for 2 hours. To catalyze the reaction, add N,N-dimethyl formamide (0.008 ml per mmol of acid) as needed. When acid chloride formation is complete, evaporate excess thionyl chloride. Remove any traces of the reagent by adding benzene and evaporating it. To ensure that solid products are relatively dense and therefore easily manipulated, carry out evaporation at an elevated temperature; a temperature not exceeding 50° C. is suitable. Wash the resulting solid with benzene and petroleum ether to give 2-(3- chlorophenylamino)pyridinyl-3-carbonylchloride, m.p. 110°-114° C.

By employing the 2-arylaminopyridinyl-3-carboxylic acid listed below in Table 5, basically the same process may be used to prepare the corresponding carbonyl chlorides thereof. The 2-arylaminopyridinyl-3-carboxylic acids that are needed to apply this method may be prepared according to U.S. Pat. No. 3,689,653.

TABLE 5

2-Arylamino-pyridyl-3-carboxylic acid

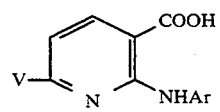

| V | Ar |
|---|---|
| H | (phenyl) |
| H | (3-CF₃-phenyl) |
| H | (3-NO₂-phenyl) |
| H | (4-F-phenyl) |
| H | (4-CH₃, Cl-phenyl) |

TABLE 5-continued

2-Arylamino-pyridyl-3-carboxylic acid

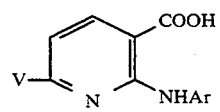

| V | Ar |
|---|---|
| CH₃ | (3-Cl-phenyl) |

EXAMPLE 5

Add equimolar amounts of the enamine, 1-acetyl-4-(1-pyrrolidino)-1,2,5,6-tetrahydropyridine (40 mmol) and triethylamine (43 mmol), both dissolved in dichloromethane (27 ml per mmol of the enamine), to a stirred, cooled solution of an equimolar amount of 2-(3-chlorophenylamino)pyridinyl-3-carbonyl chloride in dichloromethane (175 ml). When addition is complete, allow the reaction mixture to stir for 1 hour at 0° C. and for 20 hours at 25° C. Wash the organic solution with water, dilute aqueous sodium bicarbonate solution and with water. Dry the organic solution over a suitable dessicant, filter, and evaporate dichloromethane and any excess triethylamine. Crystallize the residue, 7-acetyl-10-(3-chlorophenyl)-6,8,9,10-tetrahydropyrido [2,3-b][1,6]naphthyridin-5(7H)-one, m.p. 238°-242° C. after recrystallization from CH₃CN. Alternatively, the residue may be triturated with ether, and the solid collected on a filter and then crystallized.

By employing the 2-arylaminopyridinyl-3-carboxyl chloride and enamine listed in Columns 1 and 2 of Table 6 below, the compounds listed in Column 3 thereof are prepared by basically the same procedure. If the enamine bears a methylthio group on the same carbon attached to the enamine nitrogen atom, pass nitrogen gas through the resulting solution to remove liberated methane thiol.

TABLE 6
| Col. 1 2-Arylaminopyridyl-3-carbonylchloride | | Col. 2 Enamine | Col. 3 Product[6] | Col. 4 Product m.p. °C. (solvent of crystallization) |
|---|---|---|---|---|
| Ar | V | | W = | |
| 3-Cl-C6H4 | H | 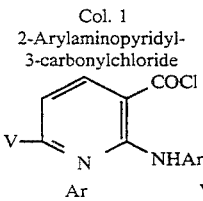 | 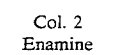 | 165–167 (CH3CN) |
| 3-CF3-C6H4 | H | 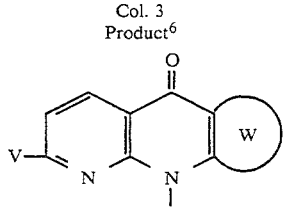 | 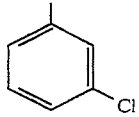 | 170–173 (CH3CN—CHCl3) |
| 3-NO2-C6H4 | H | " | " | 207–209 (CH3CN—CHCl3) |
| 3-Cl-C6H4 | H | 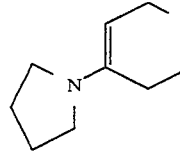 | 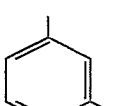 | 289–292 (CH3CN) |
| 3-Cl-C6H4 | H | 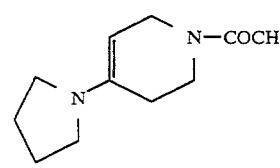 | 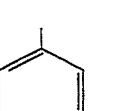 | 173–175 (CH3CN) |
| C6H5 | H | 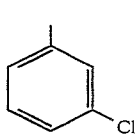 | 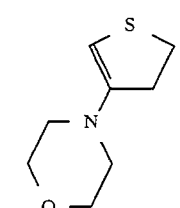 | 201.5–202.5 (C2H5OH) |
| 3-Cl-C6H4 | H | " | " | 211.0–212.0 (CH3COOH—H2O) |

5,439,916
TABLE 6-continued
| Col. 1 2-Arylaminopyridyl-3-carbonylchloride 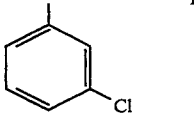 | | Col. 2 Enamine | Col. 3 Product[6] 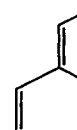 W = | Col. 4 Product m.p. °C. (solvent of crystallization) |
|---|---|---|---|---|
| Ar | V | | | |
| 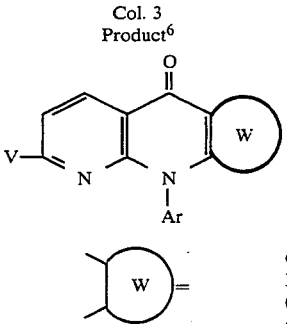 | H | 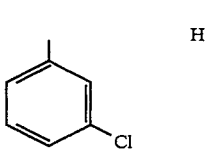 | 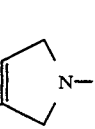 | 232–234.5 (CH$_3$CN—CHCl$_3$) |
| 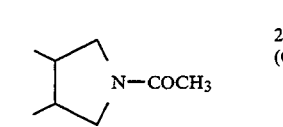 | H | 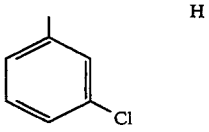 | 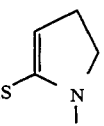 | 289–293 (CHCl$_3$—C$_2$H$_5$—OOCCH$_3$) |
| 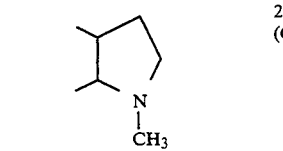 | H | 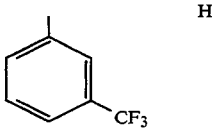 |  | 278–279 (d) (C$_2$H$_5$OH) |
| 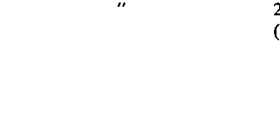 | H | " | " | 228–229.5 (d) (CH$_3$CN) |
| 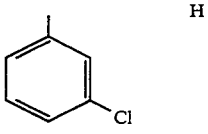 | H | 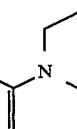 | 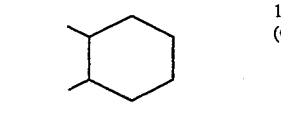 | 195–198 (CH$_3$CN) |
| 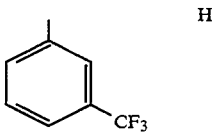 | H | 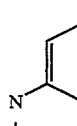 | 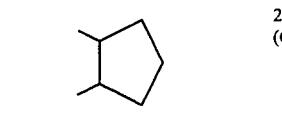 | 262–263 (CH$_3$COCH$_3$) |
| 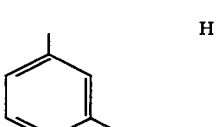 | H | " | " | 276–277 (CH$_3$CN) |

TABLE 6-continued
| Col. 1 2-Arylaminopyridyl-3-carbonylchloride Ar / V | Col. 2 Enamine | Col. 3 Product | Col. 4 Product m.p. °C. (solvent of crystallization) |
|---|---|---|---|
| 4-F-C6H4 / H | " | " | 228–229 (CH3CN) |
| 3-Cl-C6H4 / H | 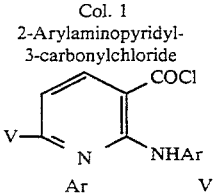 |  | 219–223 (CH3CN) |
| 4-Cl-2-CH3-C6H3 / H | 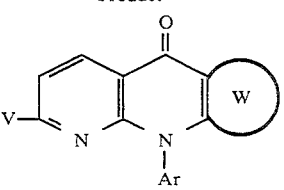 | 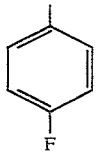 | 201–203 (CH3CN) |
| 3-Cl-C6H4 / H | 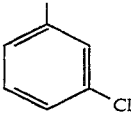 | 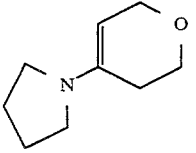 | 304–307 (d) (CHCl3—C2H5OH) |
| 3-Cl-C6H4 / H | 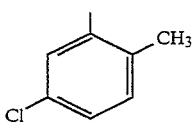 | 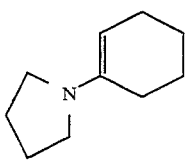 | 203–206 (CHCl3—CH3CO2C2H5) |
| 3-Cl-C6H4 / H | 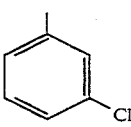 | 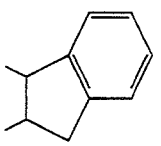 | 198–200 (CH3CN) |

TABLE 6-continued

| Col. 1<br>2-Arylaminopyridyl-<br>3-carbonylchloride<br>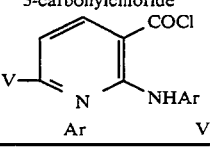 | Col. 2<br>Enamine | Col. 3<br>Product[6]<br><br>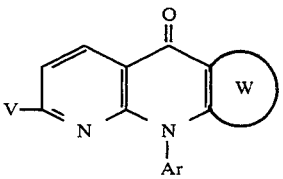 = | Col. 4<br>Product m.p. °C.<br>(solvent of<br>crystallization) |
|---|---|---|---|
| V = H<br>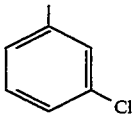 | 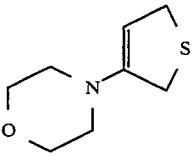 |  | 257–260<br>(CHCl₃-hexane) |
| V = CH₃<br>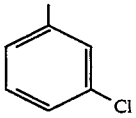 | 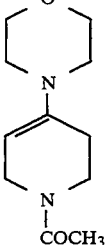 | 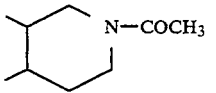 | 212–216<br>(CH₃CN) |

[6]Ar and V same as in column 1.

By employing the 2-arylaminopyridinyl-3-carboxylic chlorides and enamines listed in Columns 1 and 2 of Table 7 below, the products listed in Column 3 thereof may be prepared.

TABLE 7

| Col. 1<br>2-Arylaminopyridyl-<br>3-carbonylchloride<br>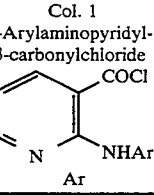 | Col. 2<br>Enamine | Col. 3<br>Product[7]<br><br>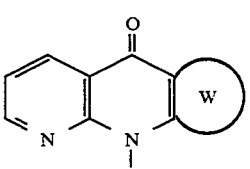 = |
|---|---|---|
| 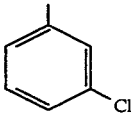 | 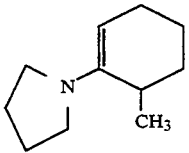 | 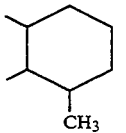 |
| 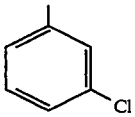 | 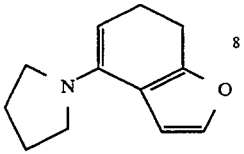[8] | 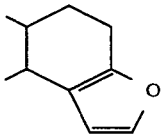 |

TABLE 7-continued

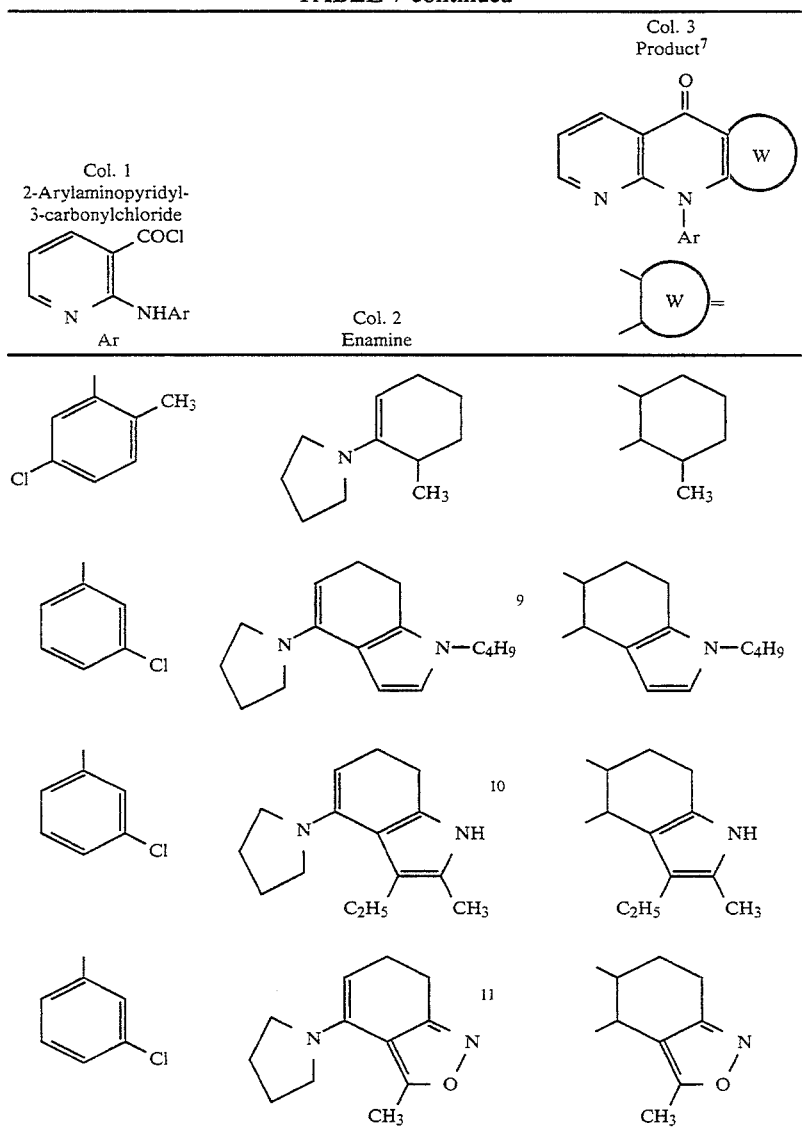

[7] Ar same as in column 1.
[8] May be prepared from the corresponding ketone described in J. Het. Chem. 21 1569 (1984).
[9] May be prepared from the corresponding ketone described Heterocycles 22 2313 (1984).
[10] May be prepared from the corresponding ketone described in Chem. Abstr. 87 68119 (1977).
[11] May be prepared from the corresponding ketone available from Aldrich Chemical Co.

EXAMPLE 6

With some compounds, the process of Example 5 may result in incomplete cyclization, i.e., intermediates of formula Ib or mixtures of such intermediates with the desired cyclized product may be produced. In such instances, the intramolecular cyclization of the intermediate to the desired product may be carried out by the following process.

The procedure of Example 4 above is repeated, except that the 2-(3-chlorophenylamino)-pyridinyl-3-carboxylic chloride and 2-(1-pyrrolidino)-indene are employed as the 2-arylaminopyridinyl-3-carbonyl chloride and enamine respectively. The intermediate product of the reaction, i.e., [2-(3-chlorophenylamino)-pyridinyl][2-(1-pyrrolidino]-1-indenyl]methanone, (or mixture with the corresponding cyclized product) is treated with paratoluenesulfonic acid basically as described in Example 1 above (but substituting the intermediate (or mixture) for the primary amine and the enaminoketone) to produce 11-(3-chlorophenyl)-10,11-dihydro-5H-indeno[2,1-b][1,8]naphthyridin-5-one, m.p.). 304°–307° C. (d) after crystallization from $C_2H_5OH$.

EXAMPLE 7

Dissolve ethyl chloroformate (0.01 mole) in $CH_2Cl_2$ (40 ml). Add the resulting solution over 30 min. to a 3° C.-solution of 2-anilinonicotinic acid (0.01 mole) and triethylamine (0.01 mole) dissolved in $CH_2Cl_2$ (400 ml). Keep the resulting solution at 3° C. for 2 hrs. to provide a solution containing 2-anilino-3-ethoxy-carbonyloxycarbonyl-pyridine. Add a solution of the enamine 3,3-dimethyl-9-(1-pyrrolidinyl)-1,5-dioxaspiro [5.5]undec-8-ene (0.01 mole) dissolved in $CH_2Cl_2$ (60 ml) over 15 min. When the last addition is complete, keep the reaction mixture at 3° C. for another 2 hrs and at 25° C. for 24 hrs. Wash the $CH_2Cl_2$ solution with aqueous NaH- CO3 solution, with water, with four portions of dilute aqueous HCl solution, and finally with water. After drying the CH2Cl2 solution, evaporate solvent to obtain the naphthyridinone, 6,8,9,10-tetrahydro-5', 5'-dimethyl-10-phenyl-spiro[benzo-[b][1,8]naphthyridin-7-(5H), 2,-[1,3]dioxan]-5-one, which is chromatographed as needed and is finally crystallized from ethyl acetate/methanol, m.p. 235.5°–238.5° C.

1-acetyl-4-(1-pyrrolidinyl)-1,2,3,6-tetrahydropyridine can be employed as the enamine to produce 7-acetyl-6,8,9,10-tetrahydro-10-phenylpyrido[2,3-b][1,6]naphthyridin-5(7H)-one, m.p. 209.5°–212.5 °, after crystallization from CH3CN.

U.S. Pat. No. 26,655 describes the commercially available (Aldrich Chemical Co.) 2-anilinonicotinic acid. The pyrrolidine enamine of 1,4-cyclohexanedione mono-2,2-dimethyltrimethylene ketal is known (*Synth. Comm.* 7, 417 (1977)), and the pyrrolidine enamine of 4-acetyl-1-piperidone is made according to *J. Am. Chem. Soc.* 76, 2029 (1954).

EXAMPLE 8

Dilute a 1M solution (73 ml) of lithium bistrimethylsilylamide in hexane with dry THF (75 ml), and add a solution of cyclopentanone (0.070 m) in THF. After brief stirring at 25° C., add a solution of methyl 2-phenylaminonicotinate (0.073 mol) in THF (48 ml). Reflux the solution for 22 hours, monitoring progress of the condensation by thin-layer chromatography.

When condensation is complete, cool the reaction mixture, evaporate solvent, and dissolve the residue in CHCl3. Wash the CHCl3 solution with water and with saturated aqueous NaCl solution. After drying the CHCl3 solution, evaporate the solvent to obtain the crude naphthyridinone. Purify the crude product by chromatography on silica gel with CHCl3, and crystallization from CH3CN to provide 6,7,8,9-tetrahydro-9-phenyl-5H-cyclopenta[b][1,8]-haphthyridin-5-one.

By employing the ketones and arylaminonicotinates indicated in Columns 1 and 2 of Table 8 below in basically the same process, the compounds listed in Column 3 are prepared. In these reactions THF or toluene are employed as solvents and lithium bistrimethylsilylamide, sodium hydride or freshly prepared sodium amide are employed as the base.

TABLE 8

| Col. 1 Ketone | $R^x$ | M | X | Ar | Col. 3 Product[12] (W) | Col. 4 Product m.p. °C. (solvent of crystallization) |
|---|---|---|---|---|---|---|
| 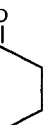 | C2H5 | N | CH | 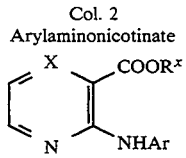 | 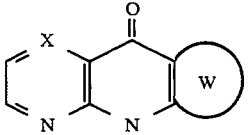 | 195–198 (CH3CN) |
| " | " | " | " | 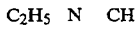 | " | 268–272 (C2H5OH) |
| " | CH3 | " | " | 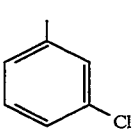 | " | 256.6–260 (CH3CN) |
| " | C2H5 | " | " | 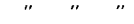 | " | 200–206 (CH3CN) |
| 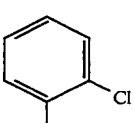 | CH3 | " | " | 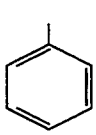 | 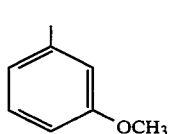 | 200–224 (CH3OH) |

TABLE 8-continued

| Col. 1 Ketone | Col. 2 Arylaminonicotinate | | | Col. 3 Product[12] | Col. 4 Product m.p. °C. (solvent of crystallization) |
|---|---|---|---|---|---|
| | $R^x$ | M | X | Ar | |
| 3,4-dihydro-1(2H)-naphthalenone | " | " | " | methylphenyl | 248–251 (C$_2$H$_5$OH) |
| benzosuberone | " | " | " | methylphenyl | 301–304.5 (C$_2$H$_5$OH) |
| " | * | | | " | 273–277 (DMF) |

[12]Ar, M and X same as in column 2.
*Made using N-phenyl isatoic anhydride, i.e., Ar in the formula of column 3 is phenyl, and M and X are both CH.

EXAMPLE 9

With some compounds, the process of Example 8 results in incomplete cyclization to the desired naphthyridinone, i.e., a 1,3-diketone (or a mixture thereof with the desired cyclized product) results (see formula Ia above). In such instances, the intramolecular cyclization to the naphythyridinone my be accomplished by subjecting the 1,3-diketone (or mixture) which results from the process of Example 8 to the following procedure.

For example, with 3,4-dihydro-6-methoxy-1-naphthalenone as the ketone and methyl 2-phenylaminonicotinate as the arylaminonicotinate, the 1,3-diketone, 3,4-dihydro-6-methoxy-2-[[2-(phenylamino)-3-pyridinyl]-carbonyl]-1-(2H)-napthalenone, results from the process of Example 8. To cyclize, reflux 9 g of the diketone in 400 ml of toluene containing a catalytic amount of p-toluenesulfonic acid. Collect the evolved water in a Dean-Stark trap. Remove the heat after 2½ hours and allow the mixture to stand overnight. Distill the toluene under vacuum on a steam bath and crystallize the residue from acetonitrile, to provide the product 5,6-dihydro-3-methoxy-12-phenylnaphtho[1,2-b][1,8]naphthyridin-7(12H)-one, m.p. 234°–237.5° C., after crystallization from CH$_3$CN.

By employing basically the same procedure and employing the ketones and arylaminonicotinates listed in Columns 1 and 2 of Table 9 below, the compounds listed in Column 3 are prepared.

TABLE 9

| Col. 1 Ketone | Col. 2 Arylaminonicotinate $R^x$ / Ar | Col. 3 Product (W ring) | Col. 4 Product m.p. °C. (solvent of crystallization) |
|---|---|---|---|
| cyclooctanone | CH₃ / phenyl | cyclooctane-fused | 197.5–201 (CH₃CN) |
| 1-indanone | " / " | indane-fused | 288–291 (CH₃CN) |
| 7-methoxy-tetralone | " / " | 7-OCH₃ tetralin-fused | 207.5–211.5 (CH₃CN) |
| 5-methoxy-tetralone | " / " | 5-OCH₃ tetralin-fused | 261–266 (DMF) |
| 6-methoxy-tetralone | " / " | 6-OCH₃ tetralin-fused | 234–238 (CH₃CN) |

EXAMPLE 10

The compound 3,4-dihydro-6-methoxy-2-[[2-(phenylamino)-3-pyridinyl]carbonyl]-1(2H)-haphthalenone, may be cyclized and dealkylated by heating 10 g of the diketone in 160 ml 48% hydrobromic acid on a steam bath with stirring for 48 hours. Remove the steam bath and stir for an additional 48 hours at ambient temperature. Pour the reaction mixture into ice water and basify with 50% sodium hydroxide solution While stirring. Collect the yellow precipitate by filtration and wash with ether. Stir the solid product in 200 ml of water and acidify the solution with glacial acetic acid. Collect the precipitated solid by filtration and wash with dilute acetic acid and then with water. Recrystallize the product 5,6-dihydro-3-hydroxy-12-phenylnaphtho[1,2-b][1,8]naphthyridin-7(12H)-one from DMF, m.p. >340° C.

Basically the same procedure is used with 3,4-dihydro-7-methoxy-2-[[2-(phenylamino)-3-pyridinyl]carbonyl]-1(2H)-naphthalenone to make 5,6-dihydro-4-hydroxy-12-phenyl-naphtho[1,2-b][1,8]naphthyridin-7(12H)-one, m.p. >330°, after crystallization from C₂H₅OH.

EXAMPLE 11

TABLE 10

| Col. 1 | Col. 2 Product | Col. 3 Product m.p. °C. (solvent of crystallization) |
|---|---|---|
| CH₃O₂C−CO₂CH₃ (cis) | (nitrone adduct with two OCH₃/C=O groups) | 197–202 (CH₃CN-Pet. ether) |
| CH₃O₂C−CO₂CH₃ (trans) | (nitrone adduct with two OCH₃/C=O groups) | 169–172 (CH₃CN-Pet. ether) |

Oxidize 10-(3-chlorophenyl)-6,7,8,9-tetrahydropyrido [2,3-b][1,6]naphthyridin-5(10H)-one with sodium tungstate and hydrogen peroxide, following the procedure of *Chem. Commun.* 874–875 (1984), to provide a mixture of a nitrone and a pyridine N-oxide which are separated by column chromatography on silica gel, each compound being eluted from the column by dichloromethane containing 2% methanol. The two compounds are 10-(3-chlorophenyl)-8,9-dihydropyrido[2,3-b][1,6]naphthyridin-5(10H)-one-7-oxide, hemihydrate (m.p. 208°–209° C. after crystallization from CH₃CN) and 10-(3-chlorophenyl)pyrido [2,3-b][1,6]-naphthyridin-5(10H)-one-7-oxide m.p. 262°–265° C. after crystallization from CHCl₃/CH₃COOC₂H₅.

EXAMPLE 12

Reflux 10-(3-chlorophenyl)-8,9dihydropyrido [2,3-b][1,6]naphthyridin-5(10H)-one-7-oxide (7.3 mmol), N-phenylmaleimide (7.4 mmol) in a solvent of ethylacetate (100 ml) and benzene (50 ml) for 15 hrs. Evaporate the solvents after filtration, and elute the residue from silca gel with chloroform. Crystallize the product, 8-(3-chlorophenyl)-6,7,13b, 13c-tetrahydro-2-phenylpyrrolo [3″, 4″:4′, 5′]isoxazolo[2′, 3′:1,2]pyrido-[4,3-b][1,8]naphthyridin-1,3,13(2H,3aH,8H)-trione, from diisopropylether/CH₃CN, m.p. 255°–258° C.

By employing the same nitrone and the compounds listed in Column 1 of Table 10 in place of N-phenylmaleimide in basically the same procedure, the compounds as listed in Column 2 of Table 10 are prepared.

By basically the same procedure as described above employing the same nitrone and the compound listed in Column 1 of Table 11 below in place of phenylmaleimide, the compounds listed in Column 2 of Table 11 may be prepared, except that the last listed compound may be prepared by the procedure described in *J. Org. Chem.* 46, 3502 (1981).

TABLE 11

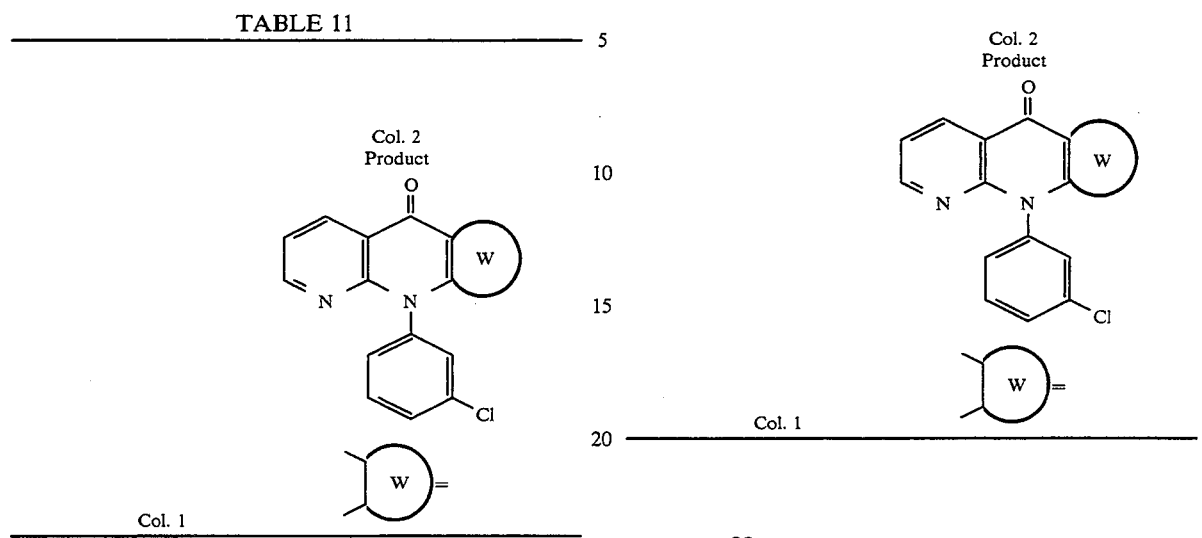

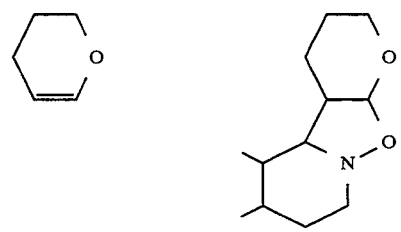

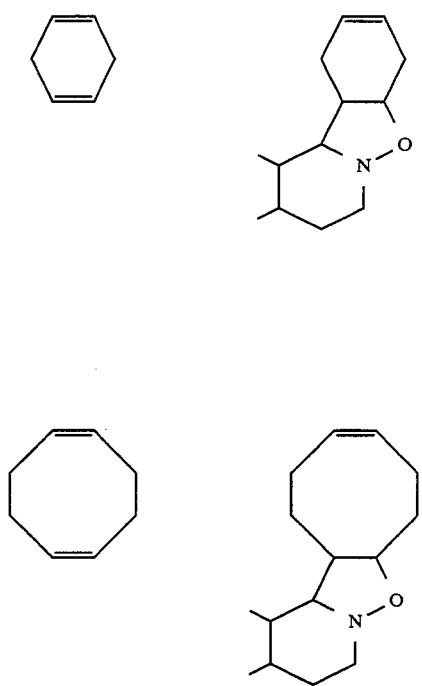

EXAMPLE 13

Charge a Paar bottle with 5,6-dihydro-3-hydroxy-12-phenyl-naphtho[1,2-b][1,8]naphthyridin-7(12H)-one, an equal weight of 5% Pd on carbon, and ethanol. Pressurize the bottle with hydrogen to about 50 psi, and shake the contents in a Paar apparatus at 25° C. Monitor the progress of hydrogenation by pressure changes or by thin-layer chromatography. When hydrogen uptake ceases, remove catalyst by filtration and ethanol by evaporation. Crystallize the residue to obtain 5,6,8,9,10,11-hexahydro-3-hydroxy-12-phenyl-naphtho[1,2-b][1,8]naphthyridin-7(12H)-one, m.p. >330° C. after crystallization from $C_2H_5OH$.

By starting with the compounds listed in Column 1 of Table 12, the compounds listed in Column 2 thereof as prepared by basically the same procedure:

TABLE 12

| Col. 1 | Col. 2 Product[18] | Col. 3 Product m.p. °C. (solvent of crystallization) |
|---|---|---|
| [structure: 1,8-naphthyridin-4(1H)-one with N-phenyl and W substituent] | [structure: 2,3-dihydro analog with NH, W substituent] | |
| W = [tetrahydronaphthalene with OCH₃] | W = [tetrahydronaphthalene with OCH₃] | 265–270 (C₂H₅OH) |
| W = [tetrahydronaphthalene] | W = [tetrahydronaphthalene] | 248.5–253 (C₂H₅OH) |
| W = [cyclopentane] | W = [cyclopentane] | 265–267 (CH₃COOC₂H₅—CH₃OH) |

EXAMPLE 14

Oxidize 6,7,8,9-tetrahydro-9-(3-methylthiophenyl)-5H-cyclopenta [b][1,8]naphthyridin-5-one with 3-chloroperbenzoic acid dissolved in CH₂Cl₂. Use one equivalent of peracid oxidant at 0°–5° C. for 5 hrs to make the corresponding sulfoxide, 6,7,8,9-tetrahydro-9-(3-methylsulfinylphenyl)-5H-cyclopenta[b][1,8]naphthyridin-5-one. Wash the reaction mixture with aqueous NaHCO₃ solution and with water. After drying the CH₂Cl₂ solution, evaporate the solvent, and chromatograph the residue on silica gel. Elute the sulfoxide with CHCl₃ containing increasing amounts of CH₃OH and crystallize the product from CH₃CN, m.p. 257°–259° C.

By basically the same reaction but employing two equivalents of the peracid oxidant at 25° C. for 50 hrs., the corresponding sulfone, 6,7,8,9-tetrahydro-9-(3-methylsulfonylphenyl)-5H-cyclopenta[b][1,8]naphthyridin-5-one is prepared, m.p 271°–273°, after crystallization from CH₃CN. Similarly, starting with 10-(3-chlorophenyl)-6,8,9,10-tetrahydro-5H-thiopyrano[4,3-b][1,8]naphthyridin-5-one or 4-(3-chlorophenyl)-2,3,4,9-tetrahydrothieno [3,2-b][1,8]naphthyridin-9-one and one equivalent of the peracid oxidant, the sulfoxides, 10-(3-chlorophenyl)-6,8,9,10-tetrahydro-5H-thiopyrano[4,3-b][1,8]naphthyridin-5-one-7-oxide (m.p. 211°–212° C. after crystallization from CH₃CN/CH₃COOC₂H₅) or 4-(3-chlorophenyl)-2,3,4,9-tetrahydrothieno [3,2-b][1,8]naphthyridin-9-one-1-oxide (m.p. 266°–267° C. after crystallization form CH₃CN), respectively, are prepared. By employing two equivalents of the peracid oxidant, the corresponding dioxides are prepared; i.e., 10-(3-chlorophenyl)-6,8,9,10-tetrahydro-5H-thiopyrano[4,3-b][1,8 ]naphthyridin-5-one-7,7-dioxide (m.p. 249°–250° C. after crystallization from CH₃CN/pet. ether) and 4-(3-chlorophenyl)-2,3,4,9-tetrahydrothieno [3,2-b][1,8]naphthyridin-9-one-1,1-dioxide (m.p. 277°–278° C. after crystallization from CHCl₃CH₃CN).

EXAMPLE 15

Reflux 6,8,9,10-tetrahydro-5′,5′-dimethyl-10-phenyl-spiro[benzo[b][1,8]naphthyridin-7-(5H) ,2′-[1,3]dioxan]-5-one (32 mmoles) with water (6 ml) and p-toluenesulfonic acid monohydrate (3.2 g) dissolved in 2-butanone (319 ml) for 3 days. Monitor the progress of hydrolysis by thin-layer chromatography. When hydrolysis is complete, cool the solution and evaporate the 2-butanone. Wash a CH₂Cl₂ solution of the residue with aqueous NaHCO₃ solution and with water. Evaporate the CH₂Cl₂ after drying the organic solution, and crystallize the residue from C₂H₅OH—CHCl₃ to obtain 6,8,9,10-tetrahydro-10-phenyl-benzo[b][1,8]naphthyridin-5,7-dione, m.p. 244°–247° C. (d).

EXAMPLE 16

Treat 5,6,8,9,10,11-hexahydro-3-methoxy-12-phenyl-naphtho [1,2-b][1,8]naphthyridin-7(12H)-one (10 mmoles) with equimolar amounts of acetyl chloride and triethylamine dissolved in CH₂Cl₂ (10 ml) at 0°–25° C. for 3 days. Wash the resulting solution with aqueous NaHCO$_3$ solution and with water, and dry the organic solution. Evaporate the CH$_2$Cl$_2$, and chromatograph the residue on silica gel. Elute the N-acetylated product with 2% MeOH in CHCl$_3$, and crystallize it from isopropyl acetate/diisopropyl ether to provide 11-acetyl-5,6,8,9,10,11-hexahydro-12-phenyl-naphtho[1,2-b][1,8]naphthyridin-7(12H)-one, m.p. 178.5°–182° C.

EXAMPLE 17

Reflux 7-acetyl-6,8,9,10-tetrahydro-10-phenylpyrido [2,3-b][1,6]naphthyridin-5(7H)-one (10.9 grams) with hot, dilute (10%) aqueous hydrochloric acid (240 ml) in 95 % ethanol (129 ml) for 8 hrs. Cool the resulting solution and collect the hydrochloride salt by filtration. If desired, the corresponding free base can be prepared by treating the hydrochloride salt with 50% aqueous sodium hydroxide solution. Crystallize the product, 6,8,9,10-tetrahydro-10-phenylpyrido [2,3-b][1,6]naphthyridin-5(7H)-one, monohydrate hydrochloride, from CH$_3$OH/C$_2$H$_5$OOCCH$_3$, m.p. 277°–279.5° C.

By employing 7-acetyl-10-(3-chlorophenyl)-6,8,9,10-tetrahydropyrido[2,3-b][1,6]naphthyridin-5(7H)-one as the acetamide (30 g) in a similar procedure, (using N HCl (445 ml) and 95 % ethanol (225 ml) for 15 hours), the product, 6,8,9,10-tetrahydro-10-(3-chlorophenyl) pyrido[2,3-b][1,8]naphthyridin-5(7H)-one may be prepared, m.p. 212°–215° C. after crystallization from CH$_2$Cl$_2$/CH$_3$COCH$_3$.

EXAMPLE 18

Charge a stainless-steel bomb with 9-(3-dimethylaminophenyl)-6,7,8,9-tetrahydro-5H-cyclopenta[b][1,8]naphthyridin-5-one (2 g), and with methyl iodide (80 ml). Close the bomb and heat it in a 140° C. oil bath for 20 hrs. Cool the bomb and contents, filter the latter, and wash the collected solid with ether to provide the product, 9-(3-trimethylammonium)-6,7,8,9-tetrahydrocyclopenta[b][1,8]naphthyridin-5-(5H)-one iodide salt, m.p. 235°–239° C., after crystallization from H$_2$O.

By a similar method 10-(3-chlorophenyl)-6,7,8,9-tetrahydropyrido[2,3-b][1,6]naphthyridin-5(10H)-one may be quaternized, using methyl iodide or ethyl iodide, respectively, to yield the products, 10-(3-chlorophenyl)-6,7,8,9-tetrahydro-7,7-dimethyl-pyrido[2,3-b][1,6]-naphthyridinium-5(10H)-one, iodide (m.p. 305°–308 ° C. after crystallization from CH$_3$OH) or 10(3-chlorophenyl)-6,7,8,9-tetrahydro-7,7-diethyl[-pyrido[4,3-b][1,8]naphthyridinium-(5(10H)-one iodide ¼ hydrate (m.p. 256°–258° C. after crystallization from CH$_3$OH—CHCl$_3$), respectively.

EXAMPLE 19

React 10-(3-chlorophenyl) -6,7,8,9tetrahydropyrido [2,3-b][1 ,6]naphthyridin-5(10H)-one (5 mmol) with benzylbromide (5.8 mmol) in acetone (40 ml) at 25° C. for 3 hours. Evaporate the acetone solvent, and elute the product from silca gel with chloroform to provide the product, 10-(3-chlorophenyl) -6,7,8,9-tetrahydro-7-N-benzyl-pyrido[2,3-b][1,6]naphthyridin-5(10H)-one, m.p. 157°–161° C. after crystallization from CH$_3$CN.

EXAMPLE 20

Oxidize 10- (3-chlorophenyl)-6,7,8,9-tetrahydropyrido[2,3-b][1,6]naphthyridin-5(10H)-one (1.6 mmol) in a refluxing solution of xylene (15 ml), using air as the oxidant and 5% Pd on C (15 mg) as the catalyst. Follow the procedure of Tetrahedron Letters 26, 1259–1260 (1985); pass air through the hot solution for 15 hours. Evaporate the xylene and elute the residue from silica gel with chloroform to provide 10-(3-chlorophenyl) pyrido[2,3-b][1,6]naphthyridin-5(10H)-one, m.p. 222°–224° C. after crystallization from CH$_3$Cl/pet. ether.

EXAMPLE 21

Saponify 7-ethoxycarbonyl-10-(3-chlorophenyl)-6,7,8,9-tetrahydrobenzo[b][1,8]naphthyridin-5(10H)-one (7.1 g) with potassium hydroxide (1.10 g) in a solvent of ethanol and water (142 ml, 9:1 by volume). After 21 hours at 25° C., add water (200 ml), cool the resulting solution in ice, and acidify (pH 2) the solution with concentrated hydrochloric acid. Collect the resulting precipitate on a filter, and crystallize it from ethanol to provide 7-carboxy-10-(3-chlorophenyl)-6,7,8,9-tetrahydrobenzo [b][1,8]naphthyridin-5(10H)-one, m.p. 279°–280.5° C.

EXAMPLE 22

Reduce 6,8,9,10-tetrahydro-10-phenylbenzo[b][1,8-]naphthyridin-5,7-dione (2 mmol) with sodium borohydride (50 mg) in a solvent of ethanol (30 ml) and water (0.25 ml). After 15 minutes, pour the reaction mixture over ice and collect the resulting precipitate on a filter. Reserve the precipitate, and extract the aqueous filtrate with chloroform. Dry the extracts, evaporate the chloroform, and combine the residue with the reserved precipitate to give the product, 10-phenyl-7-hydroxy-6,7,8,9-tetrahydro-benzo[b][1,8]naphthyridin-5(10H)-one, m.p. 283°–286° C. after crystallization from ethanol.

EXAMPLE 23

Reduce the nitro group of 6,7,8,9-tetrahydro-9-(3-nitrophenyl)-5H-cyclopenta[b][1,8]naphthyridin-5-one with stannous chloride in hydrochloric acid following the procedure of Org. Syn. (Coll. Vol. III, 1955, p. 453), precipitating the product, 9-(3-aminophenyl)-6,7,8,9-tetrahydrocyclopenta [b][1,8]naphthyridin-5(5H) -one from H$_2$O, m.p. 284.5°–285.5° C.

EXAMPLE 24

Reflux a mixture of 4-(3-chlorophenyl)-2,3-dihydrothieno[3,2-b][1,8]naphthyridin-9(9H)-one (0.11 g), ethanol (100 ml), and commercial aged Raney nickel (from 5 ml of an aqueous suspension) for 10 hours under nitrogen. Filter the resulting mixture, evaporate the solvent, and chromatograph the residue over silica gel. Elute with CHCl$_3$ to give 4-(3-chlorophenyl)-thieno[3,2-b][1,8]naphthyridin-9(4H)-one, m.p.264°–267° C. from CHCl$_3$ hexane.

EXAMPLE 25

Add a solution containing a mixture of 1-acetyl-3-(1-pyrrolidinyl)-3- and 2-pyrrolines (3.55 g) and triethylamine (2.17 g) in dichloromethane (20 ml) to a cooled, stirred suspension of 2-(3-chlorophenylamino)-pyridiny-3-carbonyl chloride (5.26 g) in an atmosphere of N$_2$. Use an ice bath for cooling. When addition is complete (30 minutes), remove the ice bath and allow stirring to continue at ambient temperature for 20 hours. Wash the resulting solution with 1M NaHCO$_3$ solution, with H$_2$O, with 1M HCland with H$_2$O. Dry the CH$_2$Cl$_2$ solution, filter it, and evaporate the CH$_2$Cl$_2$. Crystallize the residue to give 7-acetyl-9-(3-chlorophenyl) -6,7,8,9-tetrahydro-5H-pyrrolo[3,4-b][1,8]naphthyridin-5-one, m.p. 289°–293° C. from CHCl$_3$—C$_2$H$_5$OOCCH$_3$. Chromatograph the mother liquor over silica gel, and elute the column with 2% CH₃OH in CH₂Cl₂ to obtain 1-acetyl-2-[2-[(3-chlorophenyl)amino]-3-pyridiny-1-carbonyl ]-3-(1-pyrrolidinyl)-1H-pyrrole, m.p. 170°–173° C. from CH₃CN.

Reflux a mixture of 1-acetyl-2-[2-[(3-chlorophenyl)amino ]-3-pyridinylcarbonyl]-3-(1-pyrrolidinyl)-1H-pyrrole (0.45 g), p-toluenesulfonic acid monohydrate (0.21 g) in a solvent of benzene (20 ml), and tert-butanol for 12 hours. Evaporate solvent and partition the residue between CHCl₃ and 1M NaHCO₃. Wash the CHCl₃ solution with water, dry and filter the solution. Evaporate the solvent, and triturate the residue with CHCl₃ to give 4-(3-chlorophenyl)-1,4-dihydro-9H-pyrrolo[3,2-b ][1,8-]naphthyridin-9-one, m.p. 300°–301° C.

The following formulations exemplify some of the dosage forms of the compositions of this invention. In each, the term "active compound" designates 9-phenyl-6,7,8,9-tetrahydro-5H-cyclopenta[b][1,8-]naphthyridin-5-one. It is contemplated, however, that this compound may be replaced by equally effective amounts of other compounds of formula I.

PHARMACEUTICAL DOSAGE FORM EXAMPLES

Example A

Tablets

| No. | Ingredient | mg/tablet | mg/tablet |
| --- | --- | --- | --- |
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼") if needed. Dry the damp granules. Screen the dried granules if needed and mix with Item No. 4 and mix for 10–15 minutes. Add Item No. 5 and mix for 1–3 minutes. Compress the mixture to appropriate size and weight on a suitable tablet machine.

Example B

Capsules

| No. | Ingredient | mg/capsule | mg/capsule |
| --- | --- | --- | --- |
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
|  | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

Example C

Parenteral

| Ingredient | mg/vial | mg/vial |
| --- | --- | --- |
| Active Compound Sterile Powder | 100 | 500 |

Add sterile water for injection or bacteriostatic water for injection, for reconstitution,

Example D

Injectable

| Ingredient | mg/vial |
| --- | --- |
| Active Compound | 100 |
| Methyl p-hydroxybenzoate | 1.8 |
| Propyl p-hydroxybenzoate | 0.2 |
| Sodium Bisulfite | 3.2 |
| Disodium Edetate | 0.1 |
| Sodium Sulfate | 2.6 |
| Water for Injection q.s. ad | 1.0 ml |

Method of Manufacture (for 1000 vials)

1. Dissolve p-hydroxybenzoate compounds in a portion (85% of the final volume) of the water for injection at 65°–70° C.
2. Cool to 25°–35° C. Charge and dissolve the sodium bisulfite, disodium edetate and sodium sulfate.
3. Charge and dissolve active compound.
4. Bring the solution to final volume by added water for injection.
5. Filter the solution through 0.22 membrane and fill into appropriate containers.
6. Finally sterilize the units by autoclaving.

Example E

Nasal Spray

|  | mg/ml |
| --- | --- |
| Active Compound | 10.0 |
| Phenyl Mercuric Acetate | 0.02 |
| Aminoacetic Acid USP | 3.7 |
| Sorbitol Solution, USP | 57.0 |
| Benzalkonium Chloride Solution | 0.2 |
| Sodium Hydroxide 1N Solution to adjust pH | — |
| Water Purified USP to make | 1.0 ml |

The following formulations F and G exemplify some of topical dosage forms in which "Active Compound" refers to 9-(3-nitrophenyl)-6,7,8,9-tetrahydro-5H-cyclopenta [b][1,8]naphthyridin-5-one, but again other compounds of formula I may be substituted therefor.

Example F

Ointment

| Formula | mg/g |
| --- | --- |
| Active Compound | 1.0–20.0 |
| Benzyl Alcohol, NF | 20.0 |
| Mineral Oil, USP | 50.0 |
| White Petrolatum, USP to make | 1.0 g |

Method of Manufacture

Disperse active compound in a Portion of the mineral oil. Mix and heat to 65° C., a weighed quantity of white petrolatum, the remaining mineral oil and benzyl alcohol, and cool to 50°-55° C. with stirring. Add the dispersed active compound to the above mixture with Stirring. Cool to room temperature.

Example. G

Cream

| Formula | mg/g |
|---|---|
| Active Compound | 1.0-20.0 |
| Stearic Acid, USP | 60.0 |
| Glyceryl Monostearate | 100.0 |
| Propylene Glycol, USP | 50.0 |
| Polyethylene Sorbitan Monopalmitate | 50.0 |
| Sorbitol Solution, USP | 30.0 |
| Benzyl Alcohol, NF | 10.0 |
| Purified Water, USP to make | 1.0 g |

Method of Manufacture

Heat the stearic acid, glyceryl monostearate and polyethylene sorbitan monopalmitate to 70° C. In a separate vessel, dissolve sorbital solution, benzyl alcohol, water, and half quantity of propylene glycol and heat to 70° C. Add the aqueous phase to oil phase with high speed stirring. Dissolve the active compound in remaining Quantity of propylene glycol and add to the above emulsion when the temperature of emulsion is 37°–40° C. Mix uniformly with stirring and cool to room temperature.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound having the structural formula I

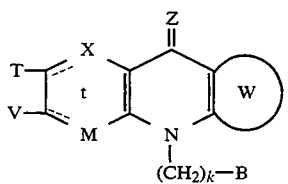

or a pharmaceutically acceptable salt or solvate thereof, wherein: in formula I:
the dotted lines (—) represent optional double bonds;
W is

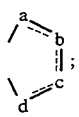

III

T and V may be the same or different and each represents H, OH, alkyl, alkoxy, phenyl or substituted phenyl;
in addition, T may also be F, Cl, or Br;
X and M must be different and each represents —CH-(R$^a$)— or —NA— when the dotted line — attached thereto does not represent a double bond; or X and M each represents =CH— or =N— when the dotted line — attached thereto represents a double bond;

with the proviso that X and M together contain one carbon atom and one nitrogen atom;
or when M is N and the dotted lines — in ring t both represent double bonds, X and T together with the carbon atom of the ring t therebetween may also represent a group

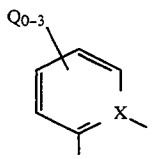

wherein X is a carbon atom and $Q_{0-3}$ represents zero, 1, 2 or 3 Q substituents as defined below;
each A is independently selected from H, alkyl, CH$_2$CH$_2$OH, COR$^b$, COOR$^e$, SO$_2$R$^b$ or (CH$_2$)$_s$R$^c$;
Z is O, S, N—R$^e$ or N(OR$^i$);
B is alkyl, alkenyl (provided k is not zero), NH$_2$, COOR$^e$, O(CO)R$^e$, or an aryl group selected from phenyl, naphthyl, indenyl, indanyl, phenanthridinyl, pyridinyl, pyrimidinyl, pyrazinyl, pyridazinyl, 1,2,4-triazinyl, furanyl, thienyl, benzofuranyl, indolyl, imidazolyl, pyrazolyl, triazolyl, or thiazolyl, any of which aryl groups may be substituted with up to three of any of the following substituents, Q: halogen, hydroxy, nitro, alkyl, CH$_2$OH, trifluoromethyl, cyano, N(R$^f$)$_2$, cycloalkyl, alkoxy, alkenyloxy, alkynyloxy, S(O)$_r$R$^e$, NHSO$_2$R$^e$, NHSO$_2$CF$_3$, NHCOCF$_3$, SO$_2$NH$_2$, SO$_2$NHR$^e$j, SO$_2$N(R$^e$)$_2$, COR$^h$,O—D—COR$^h$, or NHCOR$^d$;
R$^a$ is H, OH, alkyl, phenyl, substituted phenyl, phenylalkyl or substituted phenylalkyl;
R$^b$ is H, alkyl, phenyl, substituted phenyl, or N(R$^e$)$_2$;
R$^c$ represents carboxyl or N(R$^i$)$_2$;
R$^d$ represents H, alkyl, alkoxy, COR$^j$, or NHR$^k$;
each R$^e$ independently represents alkyl, phenyl, substituted phenyl, benzyl or substituted benzyl;
each R$^f$ independently represents H or alkyl;
R$^h$ represents OH, NH$_2$ or OR$^e$;
each R$^i$ independently represents H or alkyl;
R$^j$ represents OH or alkoxy;
R$^k$ represents H or alkyl;
D represents alkylene;
k is 0, 1 or 2;
r is 0, 1 or 2; and
s is 1, 2, 3, 4 or 5;
in formula III:
the dotted line — represents one optional double bond or two optional non-cumulated double bonds;
of the groups a, b, c and d, one of a and b is O or S(O)r, and each of the other three may be the same or different and each represents CH$_2$ or CH (if the dotted line — attached thereto represents a double bond); and
r is as defined above.

2. A compound according to claim 1, wherein k is zero, the dotted lines in ring t represent double bonds, and M represents N.

3. A compound according to claim 2, wherein T is H and Z is O.

4. A compound according to claim 3, wherein X is CH and V is H.

5. A compound according to claim 4, wherein B represents phenyl or substituted phenyl.

6. A compound according to claim 5, wherein a, c and d represent $CH_2$, the dotted lines — in formula III do not represent double bonds, and b represents O or $S(O)_r$.

7. A compound according to claim 6, wherein B represents 3-chlorophenyl, 3-methoxyphenyl, 3-methylthiophenyl or 3-nitrophenyl.

8. A compound according to claim 5 having the name:

10-(3-chlorophenyl)-6,8,9,10-tetrahydro-5H-thiopyrano[4,3-b][1,8]naphthyridin-5-one-7,7-dioxide;

10-(3-chlorophenyl)-6,8,9,10-tetrahydro-5H-thiopyrano[4,3-b][1,8]naphthyridin-5-one;

10-(3-chlorophneyl)-6,8,9,10-tetrahydro-5H-pyrano[4,3-b][1,8]naphthyridin-5-one; or 10-(3-chlorophenyl)-6,8,9,10-tetrahydro-5H-thiopyrano[4,3-b][1,8]naphthyridin-5-one-7-oxide.

9. A pharmaceutical composition which comprises an effective amount of a compound having structural formula I as defined in claim 1 in combination with a pharmaceutically acceptable carrier.

10. A method for treating allergic reactions, inflammation, peptic ulcers, hypertension or hyperproliferative skin disease in a mammal which comprises administering to said mammal an effective amount for such purpose of a compound of formula I as defined in claim 1.

11. A method for suppressing the immune response in a mammal which, comprises administering to said mammal an immunosuppressive effective amount of a compound of formula I as defined in claim 1.

* * * * *